US008063037B2

(12) United States Patent
Rewinkel et al.

(10) Patent No.: US 8,063,037 B2
(45) Date of Patent: Nov. 22, 2011

(54) PROGESTERONE RECEPTOR MODULATORS

(75) Inventors: Johannes Bernardus Maria Rewinkel, Oss (NL); Brigitte Johanna Bernita Folmer, Oss (NL); Maria Lourdes Ollero, Oss (NL); Hemen Ibrahim, Oss (NL)

(73) Assignee: N. V. Organon, Oss (NL)

( * ) Notice: Subject to any disclaimer, the term of this patent is extended or adjusted under 35 U.S.C. 154(b) by 80 days.

(21) Appl. No.: 12/115,983

(22) Filed: May 6, 2008

(65) Prior Publication Data

US 2009/0054400 A1 Feb. 26, 2009

Related U.S. Application Data

(60) Provisional application No. 60/928,013, filed on May 7, 2007.

(51) Int. Cl.
| | |
|---|---|
| *A61P 5/00* | (2006.01) |
| *A61P 15/00* | (2006.01) |
| *A61K 31/553* | (2006.01) |
| *A61K 31/554* | (2006.01) |
| *C07D 267/02* | (2006.01) |
| *C07D 281/08* | (2006.01) |

(52) U.S. Cl. .................................. 514/211.09; 540/546
(58) Field of Classification Search ............. 514/211.09; 540/546
See application file for complete search history.

(56) References Cited

U.S. PATENT DOCUMENTS

| | | | |
|---|---|---|---|
| 3,966,723 A | 6/1976 | van der Burg |
| 4,016,161 A | 4/1977 | van der Burg |
| 4,054,572 A | 10/1977 | van der Burg |
| 5,688,810 A | 11/1997 | Jones et al. |
| 7,737,136 B2 | 6/2010 | Hermkens et al. |
| 2008/0090804 A1 | 4/2008 | Rewinkel |

FOREIGN PATENT DOCUMENTS

| | | |
|---|---|---|
| DE | 2 420 168 | 4/1974 |
| EP | 0 303 306 | 2/1989 |
| EP | 0 421 802 | 4/1991 |
| EP | 0 876 815 | 11/1998 |
| WO | WO 03/084963 | 10/2003 |
| WO | WO 2006/084917 | 8/2006 |
| WO | WO 2008/037746 | 4/2008 |

OTHER PUBLICATIONS

Caulfield et al., Synthesis of 1-amino-1,2,3,14b-tetrahydro-4H-pyrido[1,2-d]dibenzo[b,f][1,4]oxazepine and Related Compounds, Journal of the Chemical Society, Perkins Transactions 1, No. 6, pp. 545-553, 1996.*
Gilman et al., The Pharmacological Basis of Therapeutics, Pergamon Press, 8$^{th}$ Edition, pp. 1397-1401, 1990.*
Beato, et al., "DNA Regulatory Elements for Steroid Hormones", J. Steroid Biochem., vol. 32, No. 5, pp. 737-748 (1989).
Caufield, et al., "Synthesis of 1-amino-1,2,3,14b-tetrahydro-4H-pyrido[1,2-d]-dibenzo[b,f] [1,4]oxazepine and related compounds", J. Chem. Soc., Perkin Trans. 1, No. 6, pp. 545-553, (1995).
Dijkema, et al., "Human Progesterone Receptor A and B Isoforms in CHO Cells. I. Stable Transfection of Receptor and Receptor-responsive Reporter Genes: Transcription Modulation by (Anti)progestagens", J. Steroid Biochem. Molec. Biol., vol. 64, No. 3-4, pp. 147-156 (1998).
Schoonen, et al., "Development of a High-Throughput in Vitro Bioassay to Assess Potencies of Progestagenic Compounds Using Chinese Hamster Ovary Cells Stably Transfected with the Human Progesterone Receptor and a Luciferase Reporter System", Analytical Biochemistry, vol. 261, pp. 222-224 (1998).
PCT International Search Report dated Aug. 6, 2003 for corresponding PCT Application No. PCT/EP03/50085.
PCT International Search Report and Written Opinion, dated Aug. 12, 2008, which was issued during the prosecution of International Application No. PCT/EP2008/003714, which corresponds to the present application.
PCT International Search Report and Written Opinion, dated Dec. 28, 2007, which was issued during the prosecution of International Application No. PCT/EP2007/060225, which corresponds to the present application.

* cited by examiner

*Primary Examiner* — Brenda Coleman
(74) *Attorney, Agent, or Firm* — Janet E. Fair; John C. Todaro

(57) ABSTRACT

The present invention provides new progesterone receptor modulators which are dibenzo[b,f]pyrido[1,2-d]oxazepine-2-amines or dibenzo[b,f]prido[1,2-d]thiazepine-2-amines, and uses thereof.

17 Claims, No Drawings

PROGESTERONE RECEPTOR MODULATORS

This application claims priority based on U.S. Provisional Patent Application No. 60/928,013, filed May 7, 2007.

The present invention relates to substituted dibenzo[b,f]pyrido[1,2-d]oxazepine-2-amines and dibenzo[b,f]pyrido[1,2-d]thiazepine-2-amines that are modulators of progesterone receptors, to their application in the field of contraception, hormone replacement therapy (HRT) or therapy of gynaecological disorders, as well as adjuvant therapy in cancer and other diseases, and to methods for the making and use of such compounds.

Intracellular receptors are a class of structurally related proteins involved in the regulation of gene transcription. Steroid receptors are a subset of these receptors, including the progesterone receptor (PR), androgen receptor (AR), estrogen receptor (ER), glucocorticoid receptor (GR) and mineralocorticoid receptor (MR). Regulation of a gene requires the intracellular receptor and a corresponding ligand which has the ability to selectively bind to the receptor in a way that affects gene transcription.

Progesterone receptor modulators (progestagens and antiprogestagens) are known to play an important role in the health of women. The natural ligand for PR is the steroid hormone progesterone, but synthetic compounds have been made which may also serve as ligands (see e.g. Jones et al., U.S. Pat. No. 5,688,810).

Progestagens are currently widely used for hormonal contraception and in HRT. Other important clinical applications of progestagens are treatment of gynaecological disorders (e.g. endometriosis, dysmenorrhea, dysfunctional uterine bleeding, severe premenstrual syndrome), breast cancer, hot flushes and mood disorders, and luteal support during IVF. In addition, they are applied in combination with other hormones and/or other therapies including, without limitation, chemotherapeutic agents such as cytotoxic and cytostatic agents, immunological modifiers such as interferons and interleukins, growth hormones or other cytokines, hormone therapies, surgery and radiation therapy.

The current steroidal progestagens have been proven to be quite safe and are well tolerated. Sometimes, however, side effects (e.g. breast tenderness, headaches, depression, and weight gain) have been reported that are attributed to these steroidal progestagens, either alone or in combination with estrogenic compounds. In addition, steroidal ligands for one receptor often show cross-reactivity with other steroidal receptors. Many steroidal progestagens also bind e.g. to the androgen receptor, whereas many antiprogestagens have affinity for the glucocorticoid receptor.

Non-steroidal progestagens have no structural similarity with steroids and therefore might be expected to display differential behaviour with respect to physicochemical properties, pharmacokinetic (PK) parameters, or tissue distribution (e.g. CNS versus peripheral), and, more importantly, may show no or less cross-reactivity to other steroid receptors. Therefore, non-steroidal progestagens may be expected to score differently on these aspects and thus offer advantages over steroidal progestagens when applied in therapy.

Dibenzo[b,f]pyrido[1,2-d][1,4]oxazepine-2-amines and dibenzo[b,f]pyrido[1,2-d][1,4]thiazepine-2-amines are known e.g. from DE 2420168. The compounds mentioned there are described as having activity on the central nervous system, especially anti-depressant activity.

Dibenzo[b,f]pyrido[1,2-d][1,4]diazepine-2-amines where the 2-amino group bears an acyl or alkylsulfonyl substituent are described in WO 2006/084917. These compounds are claimed to have agonistic, partial agonistic or antagonistic activity towards the glucocorticoid receptor.

The compounds of the present invention, however, which are dibenzo[b,f]pyrido[1,2-d][1,4]oxazepine-2-amines or dibenzo[b,f]pyrido[1,2-d][1,4]thiazepine-2-amines where the 2-amino group bears an acyl or alkylsulfonyl substituent, do not show any appreciable activity towards the glucocorticoid receptor. On the contrary, the compounds of the present invention show a considerable agonistic activity towards the progesterone receptor.

A group of non-steroidal molecules which contain a dibenzo[b,f]pyrido[1,2-d][1,4]oxazepine-1-amine, dibenzo[b,f]pyrido[1,2-d][1,4]thiazepine 1-amine, dibenzo[b,f]pyrido[1,2-d][1,4]diazepine-1-amine or dibenzo[c,f]pyrido[1,2-a]azepine-1-amine have been described as non-steroidal progesterone receptor modulators with affinity for the progesterone receptor (WO 03/084963). Progestagenic activity is described for members of all four subclasses, i.e. the oxazepine, thiazepine, diazepine and azepine subclass. It is therefore very remarkable and highly unexpected that the compounds of the present invention, being dibenzo[b,f]pyrido[1,2-d][1,4]oxazepine-2-amines and dibenzo[b,f]pyrido[1,2-d][1,4]thiazepine-2-amines, differ markedly from the dibenzo[b,f]pyrido[1,2-d][1,4]diazepine-2-amines described in WO 2006/084917, in that the oxazepines and thiazepines from the present invention show progestagenic activity but no glucocorticoid activity, whereas the compounds mentioned in WO 2006/084917 are strong modulators of the glucocorticoid receptor.

According to the present invention, (cis)-dibenzo[b,f]pyrido[1,2-d]oxazepine-2-amine and (cis)-dibenzo[b,f]pyrido[1,2-d]thiazepine-2-amine compounds are provided possessing general Formula I

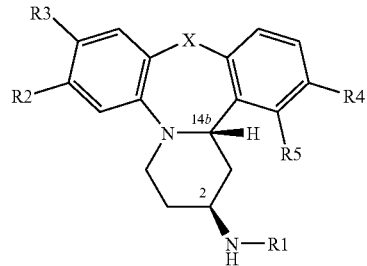

Formula I wherein
R1 is selected from the group (1-5C)acyl, (1-5C)thioacyl, (1-4C)alkylsulfonyl, and (1-4C)alkoxycarbonyl, each optionally substituted with one or more halogen atoms; and
R2 and R3 are each independently selected from the group H, halogen, cyano, nitro, or thiocarbamyl; and
R4 and R5 are each independently selected from the group H, (1-4C)alkyl, and (1-4C)alkoxy; and
X is selected from the group —O—, —S—, —SO—, and —SO$_2$—;
provided that, when R2 is Cl, R5 is not H
or a racemate thereof.

In a specific embodiment R1 is COCF$_3$. In another embodiment, R1 is COCH$_3$.

In one embodiment, R2 is H. In another embodiment, R2 is F. In yet another embodiment, R2 is Cl.

In one embodiment, R3 is CN. In another embodiment, R3 is NO$_2$. In yet another embodiment, R3 is Br.

In one embodiment, R5 is methyl. In another embodiment, R5 is methoxy.

In one embodiment, X is O.

In a specific embodiment, R1 is $COCF_3$, R2 is H, R3 is CN, R4 is H, and R5 is $CH_3$.

In yet another specific embodiment, R1 is $COCF_3$, R2 is H, R3 is CN, R4 is H and R5 is $OCH_3$.

In a further embodiment, R1 is $COCF_3$, R2 is F, R3 is CN, R4 is H, and R5 is $CH_3$.

It should be noted that in Formula I the amino substituent at position 2 and the bridgehead hydrogen substituent at position 14b are located on the same side of the ring system. This relative stereochemistry, that is the stereochemistry where the absolute orientation of one substituent is linked to the absolute orientation of another substituent, is reflected in the nomenclature of the compounds by the use of the prefix cis-.

The compounds of the subject invention are envisaged for use in therapy.

The subject invention provides a contraceptive composition comprising a compound of the subject invention and a contraceptively acceptable carrier. The subject invention also provides a pharmaceutical composition comprising a compound of the subject invention and a pharmaceutically acceptable carrier. In one embodiment, a pharmaceutical composition is envisaged for hormone replacement therapy. In another embodiment, a pharmaceutical composition is envisaged for the treatment of a gynaecological disorder.

The subject invention furthermore involves a use of a compound of the subject invention for the manufacture of a contraceptive. The subject invention also envisages a use of a compound of the subject invention for the manufacture of a medicament. In one embodiment, a use of a compound of the subject invention is for the manufacture of a medicament for hormone replacement therapy, or, in another embodiment, for the treatment of a gynaecological disorder.

The subject invention furthermore provides a method of contraception comprising administering a contraceptively effective amount of a compound of the subject invention to an individual in need thereof.

The subject invention furthermore provides a method of providing hormone replacement therapy comprising administering a pharmaceutically effective amount of a compound of the subject invention to an individual in need thereof.

The subject invention furthermore provides a method of treating a gynaecological disorder comprising administering a pharmaceutically effective amount of a compound of the subject invention to an individual in need thereof.

Compounds of Formula I can be prepared from compounds of Formula II as depicted in Scheme 1. The methods described in WO 2006/084917 for the conversion of dibenzo[b,e][1,4]diazepine derivatives into dibenzo[b,f]pyrido[1,2-d][1,4]diazepine-2-amine derivatives can also be applied to the current synthesis of compounds of Formula I from compounds of Formula II.

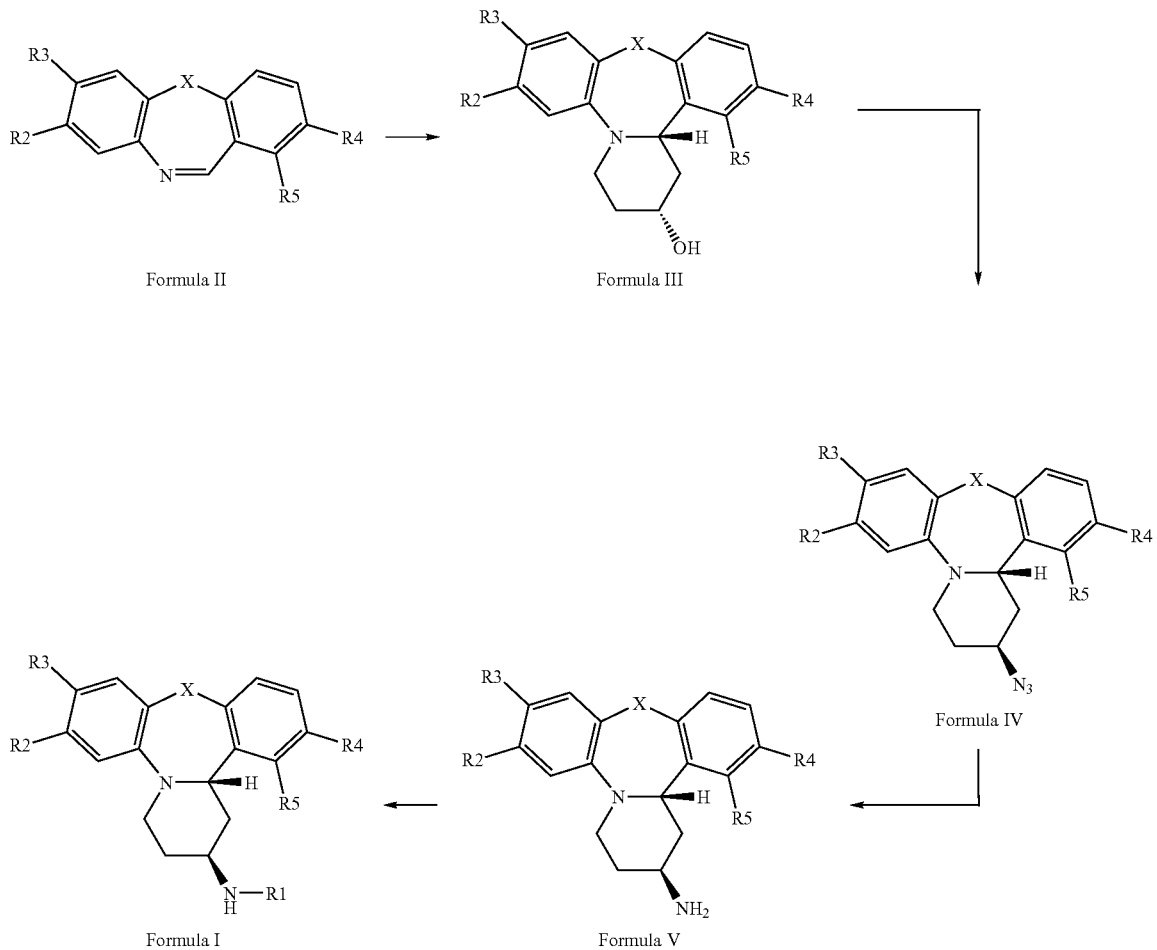

Scheme 1

Compounds of Formula II are well known in literature (e.g. WO 2003/084963). Substituents R1 through R5 can be introduced by selection of the appropriate starting materials, or by halogenation, nitration, formylation, etc., followed by further modification using the methods described below (e.g. Stille, aromatic substitution, etc.) to afford the desired compounds of Formula I possessing the desired cis stereochemistry.

The compounds of the present invention possess at least two stereogenic carbon atoms and may therefore be obtained as pure enantiomers, as a mixture of enantiomers, or as a mixture of diastereoisomers. Methods for obtaining the pure cis diastereoisomer are well known in the art, e.g. crystallisation or chromatography using straight phase or reversed phase chromatography. Also methods for obtaining the pure enantiomers are well known in the art. Such methods include, but are not limited to, chromatography using chiral columns, the use of optically pure acids such as tartaric acid or Phencyphos, or enzymatic resolution. These methods can either be applied for resolution of compounds of Formula I or for resolution of suitable intermediates in the synthesis route leading to enantiomerically pure compounds of Formula I.

The terms used in this description have the following meaning:
(1-5C)acyl is a branched or unbranched, optionally unsaturated, acyl group having 1, 2, 3, 4 or 5 C atoms, for example acetyl, butyryl, acrylyl, pivaloyl, and the like;
(1-5C)thioacyl is a branched or unbranched thioacyl group having 1, 2, 3, 4 or 5 C atoms, for example thioacetyl;
(1-4C)alkyl is a branched or unbranched alkyl group having 1, 2, 3 or 4 C atoms, for example methyl, ethyl, propyl, isopropyl, butyl, sec-butyl, tert-butyl, and the like;
(1-6C)alkyl is a branched or unbranched alkyl group having 1, 2, 3, 4, 5, or 6 C atoms, for example methyl, ethyl, propyl, isopropyl, butyl, sec-butyl, tert-butyl, pentyl, sec-pentyl, iso-pentyl, hexyl, sec-hexyl, iso-hexyl and the like;
(1-4C)alkoxy is a branched or unbranched alkoxy group having 1, 2, 3, or 4 C atoms, for example methoxy, isopropoxy, tert-butoxy, and the like;
(1-4C)alkylsulfonyl is a branched or unbranched thioacyl group having 1, 2, 3 or 4 C atoms, for example methylsulfonyl;
(1-4C)alkoxycarbonyl refers to a group of formula —CO—(1-4C)alkoxy, where (1-4C)alkoxy has the meaning given above;
Halogen refers to fluorine, chlorine, bromine or iodine.

The terms 'stereochemically pure' and 'diastereochemically pure' refer to mixtures of stereoisomers or diastereoisomers, respectively, where one of the stereochemically distinct components constitutes 95% or more of such a mixture.

For the purposes of the present invention, and according to the practices of Chemical Abstracts Service (see Naming and Indexing of Chemical Substances for CHEMICAL ABSTRACTS, the American Chemical Society, Columbus, Ohio 1987) the indication cis when naming fused polycyclic compounds such as those of the present invention shall be understood to mean the relative stereochemistry where the ring substituent in position 1 (Formula I) is located on the same side of said ring as the bridgehead substituent (which in Formula I is hydrogen) in position 14b. The meaning of the term cis will furthermore be clear to those skilled in the art from the illustrations in the various Figures, Diagrams and Reaction Schemes.

A racemate as used herein is a mixture of equal parts of enantiomers; as will be known to those skilled in the art, a racemate, also called racemic mixture or racemic preparation, is optically inactive since the optical activities of the dextrorotatory and laevorotatory enantiomers cancel out.

The progestagen receptor affinity and efficacy of the compounds according to the invention make them suitable for use in control of fertility and reproduction, e.g. in female contraception, and further for female HRT, the treatment of gynaecological disorders, as components of male contraception and in diagnostic methods focussed on the amount and/or location of progesterone receptors in various tissues. For the latter purpose it can be preferred to make isotopically labelled variants of the compounds according to the invention.

The compounds of the invention may further be useful for the treatment of endometriosis, menorrhagia, menometrorrhagia, dysmenorrhoea, acne, fibroids, osteoporosis as well as other bone disorders, bone fraction repair, sarcopenia, frailty, skin ageing, female sexual dysfunction, postmenopausal symptoms, atherosclerosis, aplastic anaemia, lipodystrophy, side effects of chemotherapy, tumours (located in e.g. breast, ovary and uterus) and others.

Suitable routes of administration for the compounds of the subject invention (also called active ingredient) are oral, rectal, nasal, topical (including transdermal, buccal and sublingual), vaginal or parenteral (including subcutaneous, intramuscular, intravenous and intradermal) administration or administration via an implant. In a specific embodiment, the compounds can be administered orally.

The exact dose and regimen of administration of the active ingredient, or a contraceptive or pharmaceutical composition thereof, will necessarily be dependent upon the therapeutic effect to be achieved (e.g. contraception, HRT) and may vary with the particular compound, the route of administration, and the age and condition of the individual subject to whom the medicament is to be administered.

A dosage for humans is likely to contain 0.0001-25 mg per kg body weight. The desired dose may be presented as one dose or as multiple sub-doses administered at appropriate intervals.

The present invention thus also relates to contraceptive and pharmaceutical compositions comprising a compound according to Formula I in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Such methods include the step of bringing in association the active ingredient with any auxiliary agent. The auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical and contraceptive compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a contraceptive and a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The compounds of the invention can also be administered in the form of devices consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in EP 303306.

The compounds of the invention can also be administered in the form of a vaginal ring such as described for example in EP 876815.

The compounds of the invention may be administered in conjunction with estrogens, androgens, progestagens, antiprogestagens, and other suitable compounds such as folic acid, vitamins, minerals etc.

EXAMPLES

The invention is further described in the following examples, which are not in any way intended to limit the scope of the inventions as claimed.

In the examples the following abbreviations are used:

$CH_2Cl_2$: dichloromethane
CuBr: copper(I) bromide
CuCN: copper(I) cyanide
CuI: copper(I) iodide
DIPEA: diisopropylethylamine
DMSO: dimethyl sulfoxide
DPPA: diphenylphosphoryl azide
e.e.: enantiomeric excess
$K_2CO_3$: potassium carbonate
M: molar
$MgSO_4$: magnesium sulfate
$NaHCO_3$: sodium hydrogencarbonate
NaOH: sodium hydroxide
$Na_2SO_4$: sodium sulfate
NBS: N-bromosuccinimide
NCS: N-chlorosuccinimide
$NH_4OH$: ammonium hydroxide
NMP: N-methylpyrrolidone
NMR: nuclear magnetic resonance
P.S. filter: Phase Separation filter
$SiO_2$: silicon dioxide (silica gel)
TBTU: O-Benzotriazol-1-yl-N,N,N',N'-tetramethyluronium tetrafluoroborate
THF: tetrahydrofuran

Example 1

Preparation of cis—N—[8-bromo-1,3,4,14b-dihydro-14-methyl-2H-dibenzo[b,f]pyrido[1,2-d][1,4]oxazepin-2-yl]-2,2,2-trifluoroacetamide (Formula I, X=O, R1=COCF$_3$, R2=H, R3=Br, R4=H, R5=CH$_3$)

a. 2-[(4-bromo-2-fluorophenyl)iminomethyl]-3-methylphenol

A solution of 4-bromo-2-fluoroaniline (19.6 g, 103.16 mmol), 2-hydroxy-6-methyl-benzaldehyde (14.03 g, 103.16 mmol) and p-toluenesulfonic acid (188 mg, 0.99 mmol) in toluene (300 mL) was heated to reflux in a Dean-Stark apparatus for 1 h and then allowed to cool to ambient temperature. After adding triethylamine (0.8 mL) the reaction mixture was concentrated to give the crude title compound (31.7 g, 99%) which was used without further purification. Data: $^1$H-NMR (400 MHz, CDCl$_3$) δ 2.52 (s, 3H), 6.72 (d, J=7.6 Hz, 1H), 6.88 (d, J=8.6 Hz, 1H), 5.15 (t, J=7.8 Hz, 1H), 7.26-7.38 (m, 3H), 9.03 (s, 1H), 13.63 (s, 1H).

b. 7-bromo-1-methyldibenz[b,f][1,4]oxazepine

To a solution of 2-[(4-bromo-2-fluorophenyl)iminomethyl]-3-methylphenol (31.7 g, 102.9 mmol) in DMSO (0.27 L), $K_2CO_3$ (28.6 g, 206.9 mmol) and 18-Crown-6 (477 mg, 1.8 mmol) were added. The resulting mixture was stirred at 140° C. for 1 h and then allowed to cool to ambient temperature. Water was added and the mixture was extracted with toluene/ethyl acetate (8:2). The combined organic layers were washed with water and with brine, dried (Na$_2$SO$_4$) and evaporated to afford the crude compound which was purified by flash chromatography (SiO$_2$, CH$_2$Cl$_2$) to give 7-bromo-1-methyldibenz[b,f][1,4]oxazepine (25.05 g, 84%). $^1$H-NMR (400 MHz, CDCl$_3$) δ 2.47 (s, 3H), 7.01 (m, 2H), 7.18-7.37 (m, 4H), 8.77 (s, 1H). (m/z)=288+290 (M+H)$^+$.

c. 8-bromo-1,14b-dihydro-14-methyl-2H-dibenzo[b,f]pyrido[1,2-d][1,4]oxazepin-2-one To a solution of 7-bromo-1-methyldibenz[b,f][1,4]oxazepine (25.05 g, 86.98 mmol) and Ytterbium(III) triflate (2.8 g, 4.5 mmol) in toluene (0.21 L) at 0° C., (E)-1-methoxy-3-trimethylsilyloxy-1,3-butadiene (18 mL, 95.7 mmol) was added dropwise. THF (0.1 L) was added to dissolve the formed precipitate and the solution was stirred for 15 min. 1N hydrochloric acid (50 mL) was added and the resulting mixture was stirred for an additional 15 min, after which it was diluted with ethyl acetate and washed with brine. After drying (Na$_2$SO$_4$) the solvent was evaporated under reduced pressure to yield the crude compound which was triturated in methanol to give the title compound (25.4 g, 82%). Data: $^1$H-NMR (400 MHz, CDCl$_3$) δ 2.31 (s, 3H), 2.43 (m, 1H), 3.00 (m, 1H), 5.23 (m, 1H), 5.41 (m, 1H), 6.99-7.52 (m, 7H). (m/z)=356+358 (M+H)$^+$.

d. (±)-trans-8-bromo-1,3,4,14b-dihydro-14-methyl-2H-dibenzo[b,f]pyrido[1,2-d][1,4]oxazepin-2-ol To a solution of the product from the previous step (22.73 g, 63.85 mmol) in THF/methanol (1:1) (1 L) at ambient temperature, NaBH$_4$ (9.6 g, 252.6 mmol) was added in portions. The resulting mixture was stirred at ambient temperature for 1 h. Saturated NH$_4$Cl solution (20 mL) was added, the solvents were concentrated, and the residue dissolved in ethyl acetate. The organic layers were washed with water, brine, dried ($Na_2SO_4$) and evaporated to afford the crude title compound (22.9 g, 99%) which was used without further purification. Data: $^1$H-NMR δ (400 MHz, $CDCl_3$) 1.71 (m, 1H), 2.08 (m, 3H), 2.30 (s, 3H), 3.16 (m, 1H), 3.72 (m, 1H), 3.9 (m, 1H), 4.16 (m, 1H), 6.79 (d, J=8.6 Hz, 1H), 6.95 (m, 1H), 7.04-7.25 (m, 4H). (m/z)=360+362 (M+H)$^+$.

e. trans-8-bromo-1,3,4,14b-dihydro-14-methyl-2H-dibenzo[b,f]pyrido[1,2-d][1,4]oxazepin-2-yl butyrate A mixture of (±)-trans-8-bromo-1,3,4,14b-dihydro-14-methyl-2H-dibenzo[b,f]pyrido[1,2-d][1,4]oxazepin-2-ol (25.89, 71.91 mmol), vinyl butyrate (80.91 g, 709 mmol) and lipase Candida Antarctica (0.855 g) in ethyl acetate (0.105 L) was stirred at ambient temperature for 3.5 h. The mixture was then filtered through dicalite and the solvent was evaporated under reduced pressure to yield the crude title compound which was purified by flash chromatography ($SiO_2$, ethyl acetate/heptane) to give the butyrate ester of one of the enantiomers of the starting material (11.7 g, 37%). Data: $^1$H-NMR (400 MHz, $CDCl_3$) δ 0.93 (m, 3H), 1.62 (m, 2H), 1.81 (m, 1H), 2.08 (m, 2H), 2.14-2.28 (m, 3H), 2.30 (s, 1H), 3.23 (m, 1H), 3.73 (m, 1H), 4.22 (d, J=11.7 Hz, 1H), 5.00 (m, 1H), 6.80 (d, J=8.2 Hz, 1H), 6.94 (m, 1H), 7.03-7.26 (m, 4H). (m/z)= 430+432 (M+H)$^+$.

f. trans-8-bromo-1,3,4,14b-dihydro-14-methyl-2H-dibenzo[b,f]pyrido[1,2-d][1,4]oxazepin-2-ol A mixture of the homochiral butyrate obtained in the previous step (11.7 g, 27.21 mmol) and 2M aqueous NaOH (13.3 mL) in (110 mL) THF/ethanol (1:3) was stirred at ambient temperature for 3 h. It was then diluted with ethyl acetate, washed with brine, dried ($Na_2SO_4$) and evaporated to afford the crude compound which was purified by flash chromatography ($SiO_2$, ethyl acetate/heptane) to give one of the enantiomers of trans-8-bromo-1,3,4,14b-dihydro-14-methyl-2H-dibenzo[b,f]pyrido[1,2-d][1,4]oxazepin-2-ol (9.54 g, 97%). Data: (ee=99%) (chiralpak AS-25*0.46 cm, heptane:ethanol=9:1). $^1$H-NMR (400 MHz, $CDCl_3$) δ 1.71 (m, 1H), 2.08 (m, 3H), 2.30 (s, 3H), 3.16 (m, 1H), 3.72 (m, 1H), 3.9 (m, 1H), 4.16 (m, 1H), 6.79 (d, J=8.6 Hz, 1H), 6.95 (m, 1H), 7.04-7.25 (m, 4H). (m/z)=360+362 (M+H)$^+$.

g. cis-2-azido-8-bromo-1,3,4,14b-dihydro-14-methyl-2H-dibenzo[b,f]pyrido[1,2-d][1,4]oxazepine To a solution of trans-8-bromo-1,3,4,14b-dihydro-14-methyl-2H-dibenzo[b,f]pyrido[1,2-d][1,4]oxazepin-2-ol (9.54 g, 26.5 mmol) in THF (150 mL) at 0° C., triphenylphosphine (9.0 g, 34.4 mmol) and diisopropylazodicarboxylate (7.14 g, 34.4 mmol) were added and stirred for 5 min. Diphenylphosphoryl azide (9.52 ml, 34.4 mmol) was added. The reaction was allowed to warm to ambient temperature and stirred for 3 h. The reaction mixture was concentrated under reduced pressure and the crude product was purified by column chromatography ($SiO_2$, Toluene) to give the title azide (10.01 g, 98%). Data: $^1$H-NMR (400 MHz, $CDCl_3$) δ 1.86 (m, 2H), 2.06 (m, 1H), 2.33 (s, 3H), 2.39 (m, 1H), 3.48 (m, 2H), 4.18 (m, 1H), 4.57 (m, 1H), 6.80 (d, J=8.2 Hz, 1H), 6.95 (m, 1H), 7.03-7.28 (m, 4H).

h. cis-8-bromo-1,3,4,14b-dihydro-14-methyl-2H-dibenzo[b,f]pyrido[1,2-d][1,4]oxazepine-2-amine To a cold solution of copper(II) sulfate (5.24 g, 33.5 mmol) and $NaBH_4$ (4 g, 105 mmol) in methanol, the azide obtained in the previous step (10.01 g, 26 mmol) in THF (50 mL) was added dropwise. An additional amount of $NaBH_4$ (4 g, 105 mmol) was added in portions. The resulting mixture was stirred for 4 h. 6N Hydrochloric acid was added and the mixture stirred overnight at ambient temperature. The reaction mixture was concentrated under reduced pressure, dissolved in diethyl ether, washed with 2N aqueous NaOH and with brine, dried ($Na_2SO_4$) and evaporated to afford the crude compound which was purified by flash chromatography ($SiO_2$, ethyl acetate/ethanol) to give cis-8-bromo-1,3,4,14b-dihydro-14-methyl-2H-dibenzo[b,f]pyrido[1,2-d][1,4]oxazepine-2-amine (5.2 g, 55%). Data: (m/z)=359+361 (M+H)$^+$.

i. (−)-cis—N—[8-bromo-1,3,4,14b-dihydro-14-methyl-2H-dibenzo[b,f]pyrido[1,2-d][1,4]oxazepin-2-yl]-2,2,2-trifluoroacetamide A mixture of the amine obtained from the previous step (5.2 g, 14.48 mmol), ethyl trifluoroacetate (12.3 g, 72.4 mmol) and triethylamine (7.41 g, 72.4 mmol) in methanol (200 mL) was stirred overnight at ambient temperature. The reaction mixture was concentrated to give the crude title compound (6.58 g, 98%) which was used without further purification. Data: $^1$H-NMR (400 MHz, $CDCl_3$) δ 1.90 (m, 1H), 2.08 (m, 1H), 2.20 (s, 3H), 2.21-2.38 (m, 2H), 3.30 (m, 1H), 3.59 (m, 1H), 4.26 (m, 1H), 4.41 (m, 1H), 6.55 (br, 1H), 6.81 (d, J=8.2 Hz, 1H), 6.93 (m, 1H), 7.07-7.27 (m, 4H). (m/z)=455+457 (M+H)$^+$.

Example 2

Preparation of (−)-cis—N—[8-cyano-1,3,4,14b-dihydro-14-methyl-2H-dibenzo[b,f]pyrido[1,2-d][1,4] oxazepin-2-yl]-2,2,2-trifluoroacetamide (Formula I, X=O, R1=$COCF_3$, R2=H, R3=CN, R4=H, R5=$CH_3$)

A mixture of cis—N—[8-bromo-1,3,4,14b-dihydro-14-methyl-2H-dibenzo[b,f]pyrido[1,2-d][1,4]oxazepin-2-yl]-2,2,2-trifluoroacetamide (6.4 g 14.06 mmol), CuCN (3.14 g, 35.06 mmol), CuI (0.286 g, 1.5 mmol) and NMP 40 mL was stirred with cooling in the microwave for 20 min. at 180° C., 300 Watt. After cooling down, the reaction mixture was poured into water (500 mL). The precipitate, containing product and salts, was redissolved in ethyl acetate and the salts were filtered off. The organic layer was washed with $NH_4OH$-solution, water, and brine, dried, and concentrated to give the crude compound which was purified by flash chromatography ($SiO_2$, $CH_2Cl_2$) and crystallized from acetonitrile to give cis—N—[8-cyano-1,3,4,14b-dihydro-14-methyl-2H-dibenzo[b,f]pyrido[1,2-d][1,4]oxazepin-2-yl]-2,2,2-trifluoroacetamide (2.2 g, 39%). Data: (levorotatory), e.e.=100% (chiralpak AD-H 25*0.46 cm, heptane:ethanol=8:2). $^1$H-NMR (400 MHz, $CDCl_3$) δ 1.91 (m, 1H), 2.04 (m, 1H), 2.22 (m, 1H), 2.24 (s, 3H), 2.53 (m, 1H), 3.45 (m, 1H), 3.80 (m, 1H), 4.43 (m, 1H), 4.48 (m, 1H), 6.59 (br, 1H), 6.90 (d, J=8.2 Hz, 1H), 6.98 (m, 1H), 7.07-7.39 (m, 4H). MIM=401.

Example 3

Preparation of (−)-cis—N—[8-cyano-1,3,4,14b-dihydro-14-methyl-2H-dibenzo[b,f]pyrido[1,2-d][1,4]oxazepin-2-yl]acetamide (Formula I, X=O, R1=COCH$_3$, R2=H, R3=CN, R4=H, R5=CH$_3$)

a. cis-2-amino-1,3,4,14b-dihydro-14-methyl-2H-dibenzo[b,f]pyrido[1,2-d][1,4]oxazepine-8-carbonitrile A solution of the product of example 2 (2.7 g, 6.73 mmol) and K$_2$CO$_3$ (3.32 g, 24 mmol) in methanol/water (5:1) (288 mL) was stirred at 90° C. for 3 h. The reaction mixture was concentrated and extracted with ethyl acetate. The combined organic layers were washed with water, brine, dried (Na$_2$SO$_4$) and concentrated to afford the crude title compound (2.05 g, 99%) which was used without further purification. Data: $^1$H-NMR (400 MHz, CDCl$_3$) δ 1.54 (m, 2H), 2.02 (m, 1H), 2.36 (s, 3H), 2.57 (m, 1H), 3.64 (m, 2H), 3.76 (m, 1H), 5.02 (m, 1H), 6.89 (d, J=8.2 Hz, 1H), 6.98 (m, 1H), 7.03-7.35 (m, 4H).

b. (−)-cis—N—[8-cyano-1,3,4,14b-dihydro-14-methyl-2H-dibenzo[b,f]pyrido[1,2-d]1,4]oxazepin-2-yl]acetamide A mixture of the product obtained in the previous step (2.05 g, 6.7 mmol), acetic anhydride (1.02 g, 10 mmol) and pyridine (1.06 g, 13.5 mmol) in CH$_2$Cl$_2$ was stirred at ambient temperature for 4 h. The reaction mixture was poured into saturated (aq) NaHCO$_3$ solution, the organic layer was separated, washed with brine, dried (Na$_2$SO$_4$) and evaporated to afford the crude compound which was purified by flash chromatography (SiO$_2$, CH$_2$Cl$_2$/ethanol) and crystallized from acetonitrile/water to give (−)-cis—N—[8-cyano-1,3,4,14b-dihydro-14-methyl-2H-dibenzo[b,f]pyrido[1,2-d][1,4]oxazepin-2-yl]acetamide (0.54 g, 23%). Data: e.e.=100% (chiralpak AS-H 25*0.46 cm, heptane: ethanol=8:2). $^1$H-NMR (400 MHz, CDCl$_3$) δ 1.81 (m, 1H), 1.19 (m, 1H), 2.10 (s, 3H), 2.26 (s, 3H), 2.44 (m, 1H), 3.42 (m, 1H), 3.73 (m, 1H), 4.37 (m, 1H), 4.50 (m, 1H), 5.78 (br, 1H), 6.89 (d, J=8.2 Hz, 1H), 6.96 (m, 1H), 7.10 (m, 2H), 7.30 (m, 1H), 7.35 (d, J=20 Hz, 1H). MIM=347. [α]$_D^{20}$=−524° (c=1.00, THF).

Example 4

Preparation of (±)-cis—N—[7-fluoro-1,3,4,14b-dihydro-14-methyl-2H-dibenzo[b,f]pyrido[1,2-d][1,4]oxazepin-2-yl]-2,2,2-trifluoroacetamide (Formula I, X=O, R1=COCF$_3$, R2=F, R3=R4=H, R5=CH$_3$)

a. 2-[(2,5-difluorophenyl)iminomethyl]-3-methylphenol

Preparation analogous to Example 1, step a, from 2,5-difluoroaniline (11.33 g, 113 mmol) gave the title compound (27.9 g, 100%). Data: $^1$H-NMR (400 MHz, CDCl$_3$) 2.53 (s, 3H), 6.72 (d, J=7.8 Hz, 1H), 6.86-7.32 (m, 5H), 9.01 (s, 1H), 13.6 (br, 1H).

b. 8-fluoro-1-methyldibenz[b,f][1,4]oxazepine

Preparation analogous to Example 1, step b, from 2-[(2,5-difluorophenyl)iminomethyl]-3-methylphenol (27.9 g, 113 mmol) gave the title compound (25 g, 97%). Data: (m/z)=228 (M+H)$^+$.

c. 7-fluoro-1,14-b-dihydro-14-methyl-2H-dibenzo[b,f]pyrido[1,2-d][1,4]oxazepin-2-one Preparation analogous to Example 1, step c, from the oxazepine from the previous step (25 g, 110 mmol) and Scandium triflate (2.8 g, 5.69 mmol) gave the crude compound which was purified by flash chromatography (SiO$_2$, toluene) to give 7-fluoro-1,14b-dihydro-14-methyl-2H-dibenzo[b,f]pyrido[1,2-d][1,4]oxazepin-2-one (10.3 g, 31%). Data: (m/z)= 296 (M+H)$^+$.

d. (±)-trans-7-fluoro-1,3,4,14b-dihydro-14-methyl-2H-dibenzo[b,f]pyrido[1,2-d][1,4]oxazepin-2-ol Preparation analogous to Example 1, step d, from 7-fluoro-1,14b-dihydro-14-methyl-2H-dibenzo[b,f]pyrido[1,2-d][1,4]oxazepin-2-one (10.3 g, 34.91 mmol) gave the title compound (10.4 g, 99%). Data: (m/z)=300 (M+H)$^+$.

e. (±)-cis-2-azido-7-fluoro-1,3,4,14b-dihydro-14-methyl-2H-dibenzo[b,f]pyrido[1,2-d][1,4]oxazepine Preparation analogous to Example 1, step g, from the product of the previous step (10.4 g, 34.78 mmol) gave the title compound (6.8 g, 60%). Data: (m/z)=325 (M+H)$^+$.

f. (±)-cis-7-fluoro-1,3,4,14b-dihydro-14-methyl-2H-dibenzo[b,f]pyrido[1,2-d][1,4]oxazepine-2-amine A solution of AlCl$_3$ (5.9 g, 44.2 mmol) in diethyl ether (80 mL) was added to a solution of LiAlH$_4$ (2.61 g, 68.8 mmol) in diethyl ether (80 mL). After 30 min a solution of (±)-cis-2-azido-7-fluoro-1,3,4,14b-dihydro-14-methyl-2H-dibenzo[b,f]pyrido[1,2-d][1,4]oxazepine (6.82 g, 21.03 mmol) in THF (150 mL) was added and the reaction was stirred at ambient temperature for 1 h. The reaction was quenched by adding 4N aqueous NaOH (30 mL) dropwise, the formed salts were filtered off and the filtrate was concentrated under reduced pressure to give the title amine (5.1 g, 81%). Data: (m/z)=299 (M+H)$^+$.

g. (±)-cis—N—[7-fluoro-1,3,4,14b-dihydro-14-methyl-2H-dibenzo[b,f]pyrido[1,2-d][1,4]oxazepin-2-yl]-2,2,2-trifluoroacetamide Preparation analogous to Example 1, step i, from (±)-cis-7-fluoro-1,3,4,14b-dihydro-14-methyl-2H-dibenzo[b,f]pyrido[1,2-d][1,4]oxazepine-2-amine (2.4 g, 8.04 mmol) gave the title compound (3.17 g, 99%). Data: (m/z)=395 (M+H)$^+$.

Example 5

Preparation of (±)-cis—N—[8-bromo-7-fluoro-1,3,4,14b-dihydro-14-methyl-2H-dibenzo[b,f]pyrido[1,2-d][1,4]oxazepin-2-yl]-2,2,2-trifluoroacetamide (Formula I, X=O, R1=COCF$_3$, R2=F, R3=Br, R4=H, R5=CH$_3$)

To a solution of (±)-cis—N—[7-fluoro-1,3,4,14b-dihydro-14-methyl-2H-dibenzo[b,f]pyrido[1,2-d][1,4]oxazepin-2- yl]-2,2,2-trifluoroacetamide (3.17 g, 8.03 mmol) in THF (100 mL) were added NBS (1.78 g, 10.0 mmol) and 6N hydrochloric acid (1.67 mL, 10 mmol), and the resulting mixture stirred at ambient temperature for 4 h. The reaction mixture was poured into water and extracted with ethyl acetate. The combined organic layers were washed brine, dried ($Na_2SO_4$) and evaporated to afford the crude compound which was purified by flash chromatography ($SiO_2$, heptane/ethyl acetate) to give (±)-cis—N—[8-bromo-7-fluoro-1,3,4,14b-dihydro-14-methyl-2H-dibenzo[b,f]pyrido[1,2-d][1,4]oxazepin-2-yl]-2,2,2-trifluoroacetamide (1.39 g, 35%). Data: $^1$H-NMR (400 MHz, $CDCl_3$) δ 1.87-1.95 (m, 1H), 2.03-2.09 (m, 1H), 2.20 (s, 3H), 2.20-2.42 (m, 2H), 3.30 (dt, J=3 and 13 Hz, 1H), 3.55-3.62 (m, 1H), 4.30 (dd, J=2 and 12 Hz, 1H), 4.41 (br, 1H), 6.53 (br, 1H), 6.68 (d, J=11 Hz, 1H), 6.92-6.95 (m, 1H), 7.05-7.13 (m, 2H), 7.26 (d, J=7 Hz, 1H). Data: (m/z)=473 (M+H)$^+$.

Example 6

Preparation of (±)-cis—N—[8-cyano-7-fluoro-1,3,4,14b-dihydro-14-methyl-2H-dibenzo[b,f]pyrido[1,2-d][1,4]oxazepin-2-yl]-2,2,2-trifluoroacetamide (Formula I, X=O, R1=COCF$_3$, R2=F, R3=CN, R4=H, R5=CH$_3$)

Preparation analogous to Example 2, from the bromide obtained in the previous example (1.39 g, 2.93 mmol). The crude compound was crystallized from heptane/ethyl acetate and gave the title compound (0.53 g, 18%). Data: $^1$H-NMR (400 MHz, CDCl$_3$) δ 1.88-1.97 (m, 1H), 2.01-2.07 (m, 1H), 2.18-2.28 (m, 1H), 2.25 (s, 3H), 2.52-2.60 (m, 1H), 3.42-3.51 (m, 1H), 3.73-3.80 (m, 1H), 4.43 (brs, 1H), 4.51-4.55 (m, 1H), 6.51 (br, 1H), 6.62 (d, J=11 Hz, 1H), 6.96-7.00 (m, 1H), 7.05-7.09 (m, 1H), 7.14-7.18 (m, 1H), 7.28 (d, J=6 Hz, 1H). Data: (m/z)=420 (M+H)$^+$.

Example 7

Preparation of (±)-cis—N—[8-cyano-7-fluoro-1,3,4,14b-dihydro-14-methyl-2H-dibenzo[b,f]pyrido[1,2-d][1,4]oxazepin-2-yl]acetamide (Formula I, X=O, R1=COCH$_3$, R2=F, R3=CN, R4=H, R5=CH$_3$)

a. (±)-cis-2-amino-7-fluoro-1,3,4,14b-dihydro-14-methyl-2H-dibenzo[b,f]pyrido[1,2-d][1,4]oxazepine-8-carbonitrile To a stirred solution of the product of Example 6 (0.6 g, 1.43 mmol) in THF (10 ml) at 0° C. was added lithium hydroxide monohydrate (8.58 mmol, 8.58 ml) dropwise, and the reaction was stirred overnight at ambient temperature. It was then diluted with ethyl acetate and washed with brine, dried (Na$_2$SO$_4$) and evaporated to afford the crude title compound (0.438 g, 95%) which was used without further purification. Data: (m/z)=324 (M+H)$^+$.

b. (±)-cis—N—[8-cyano-7-fluoro-1,3,4,14b-dihydro-14-methyl-2H-dibenzo[b,f]pyrido[1,2-d][1,4]oxazepin-2-yl]acetamide Preparation analogous to Example 3, step b, from the amine obtained in the previous step (0.438 g, 1.354 mmol). The crude compound was crystallized from heptane/ethyl acetate to give the title compound (0.272 g, 55%). Data: $^1$H-NMR (400 MHz, CDCl$_3$) δ 1.83 (m, 1H), 1.98 (m, 1H), 2.09 (s, 3H), 2.13 (m, 1H), 2.27 (s, 3H), 2.47 (m, 1H), 3.45 (m, 1H), 3.70 (m, 1H), 4.36 (m, 1H), 4.57 (m, 1H), 5.88 (br, 1H), 6.58 (d, J=11.6 Hz, 1H), 6.97 (d, J=7.0 Hz, 1H), 7.05 (d, J=7.0 Hz, 1H), 7.14 (t, J=7.0 Hz, 1H), 7.25 (d, J=6.2 Hz, 1H). (m/z)=366 (M+H)$^+$.

Example 8

Preparation of (±)-cis—N—[8-bromo-1,3,4,14b-dihydro-14-methoxy-2H-dibenzo[b,f]pyrido[1,2-d][1,4]oxazepin-2-yl]-2,2,2-trifluoroacetamide (Formula I, X=O, R1=COCF$_3$, R2=H, R3=Br, R4=H, R5=CH$_3$O)

a. 2-[(4-bromo-2-fluorophenyl)iminomethyl]-3-methoxyphenol

Preparation analogous to Example 1, step a, from 4-bromo-2-difluoroaniline (11.24 g, 59.15 mmol) and 2-hyroxy-6-methoxybenzaldehyde (9 g, 59.12 mmol) gave the title compound (19.16 g, 100%). Data: $^1$H-NMR (400 MHz, CDCl$_3$) δ 3.38 (s, 3H), 6.38 (d, J=8.1 Hz, 1H), 6.61 (d, J=8.1 Hz, 1H), 7.13-7.36 (m, 4H), 9.17 (s, 1H), 13.78 (s, 1H).

b. 7-bromo-1-methoxydibenz[b,f][1,4]oxazepine

To a solution of the phenol obtained in the previous step (19.16 g, 59.16 mmol) in DMF (88 mL), Cs$_2$CO$_3$ (22 g, 67.5 mmol) was added. The resulting mixture was stirred at 70° C. for 3 h and then allowed to cool to ambient temperature. Water was added and the product was collected by filtration, washed with water and dried under reduced pressure to yield the title compound, which was used without further purification (17.8 g, 99%). Data: $^1$H-NMR (400 MHz, CDCl$_3$) δ 3.87 (s, 3H), 6.72 (m, 2H), 7.19 (d, J=8.2 Hz, 1H), 7.29 (m, 2H), 7.40 (t, J=8.2 Hz, 1H), 8.78 (s, 1H). (m/z)=304+306 (M+H)$^+$.

c. 8-bromo-1,14b-dihydro-14-methoxy-2H-dibenzo[b,f]pyrido[1,2-d][1,4]oxazepin-2-one Preparation analogous to Example 1, step c, from 7-bromo-1-methoxydibenz[b,f][1,4]oxazepine (17.8 g, 58.55 mmol) gave the crude compound which was crystallized from toluene to give the title compound (10.3 g, 31%). $^1$H-NMR (400 MHz, CDCl$_3$) δ 2.75 (m, 1H), 2.88 (m, 1H), 3.79 (s, 3H), 5.37 (m, 1H), 5.46 (dd, J=12.7 Hz and 4.0 Hz, 1H), 6.71 (m, 1H), 6.91 (m, 1H), 7.06 (d, J=8.9 Hz, 1H), 7.19-7.43 (m, 3H). (m/z)=372+374 (M+H)$^+$.

d. (±)-trans-8-bromo-1,3,4,14b-dihydro-14-methoxy-2H-dibenzo[b,f]pyrido[1,2-d][1,4]oxazepin-2-ol Preparation analogous to Example 1, step d, from the product of the previous step (23 g, 62 mmol) gave the title compound (14 g, 61%). Data: $^1$H-NMR (400 MHz, CDCl$_3$) δ 1.73 (m, 1H), 1.86 (q, J=11.6 Hz, 1H), 2.10 (m, 1H), 2.27 (m, 1H), 3.12 (dt, J=11.6 Hz and 2.7 Hz), 3.56 (m, 1H), 3.79 (s, 3H), 3.91 (m, 1H), 4.28 (dd, J=10.8 Hz and 1.5 Hz, 1H), 6.65 (m, 1H), 6.82 (d, J=8.1 Hz, 1H), 6.68 (m, 1H), 7.15 (m, 2H), 7.24 (d, J=2.0 Hz, 1H).

e. (±)-cis-2-azido-8-bromo-1,3,4,14b-dihydro-14-methoxy-2H-dibenzo[b,f]pyrido[1,2-d][1,4]oxazepine Preparation analogous to Example 1, step g, from (±)-trans-8-bromo-1,3,4,14b-dihydro-14-methoxy-2H-dibenzo[b,f]pyrido[1,2-d][1,4]oxazepin-2-ol (12 g, 32.24 mmol) gave the title compound (9.3 g, 71%). Data: $^1$H-NMR (400 MHz, CDCl$_3$) δ 1.82 (m, 1H), 2.03 (m, 1H), 2.13 (m, 1H), 2.25 (m, 1H), 3.30 (m, 1H), 3.40 (dt, J=11.6 Hz and 2.3 Hz, 1H), 3.80 (s, 3H), 4.13 (m, 1H), 4.61 (dd, J=10.4 Hz and 1.9 Hz, 1H), 6.65 (m, 1H), 6.85 (m, 2H), 7.16 (m, 2H), 7.24 (m, 1H). (m/z)=401+403 (M+H)$^+$.

f. (±)-cis-8-bromo-1,3,4,14b-dihydro-14-methoxy-2H-dibenzo[b,f]pyrido[1,2-d][1,4]oxazepine-2-amine Preparation analogous to Example 1, step h, from the azide obtained in the previous step (9.3 g, 23.19 mmol) gave the title compound (7.46 g, 85%). Data: (m/z)=375+377 (M+H)$^+$.

g. (±)-cis—N—[8-bromo-1,3,4,14b-dihydro-14-methoxy-2H-dibenzo[b,f]pyrido[1,2-d][1,4]oxazepin-2-yl]-2,2,2-trifluoroacetamide Preparation analogous to Example 1, step i, from the amine obtained in the previous step (7.46 g, 19.89 mmol) gave the title compound (8.95 g, 95%). Data: (m/z)=471+473 (M+H)$^+$.

Example 9

Preparation of (±)-cis—N—[8-cyano-1,3,4,14b-dihydro-14-methoxy-2H-dibenzo[b,f]pyrido[1,2-d][1,4]oxazepin-2-yl]-2,2,2-trifluoroacetamide (Formula I, X=O, R1=COCF$_3$, R2=H, R3=CN, R4=H, R5=CH$_3$O)

Preparation analogous to Example 2, from the product obtained in the previous step (8.95 g, 19 mmol). The crude compound was crystallized from acetonitrile/water and gave (±)-cis—N—[8-cyano-1,3,4,14b-dihydro-14-methoxy-2H-dibenzo[b,f]pyrido[1,2-d][1,4]oxazepin-2-yl]-2,2,2-trifluoroacetamide (6.9 g, 87%). Data: $^1$H-NMR (400 MHz, DMSO) δ 1.83 (m, 1H), 1.92-2.18 (m, 4H), 3.54 (m, 1H), 4.20 (m, 1H), 4.71 (m, 1H), 6.83 (d, J=8.1 Hz, 1H), 6.92 (d, J=8.1 Hz, 1H), 7.11 (d, J=8.5 Hz, 1H), 7.24 (t, J=8.1 Hz, 1H), 7.50 (dd, J=8.1 Hz and 2.0 Hz, 1H), 7.58 (d, J=2.0 Hz, 1H), 9.55 (br, 1H). (m/z)=418 (M+H)$^+$.

Example 10

Preparation of (±)-cis—N—[7-chloro-1,3,4,14b-dihydro-14-methoxy-2H-dibenzo[b,f]pyrido[1,2-d][1,4]oxazepin-2-yl]-2,2,2-trifluoroacetamide (Formula I, X=O, R1=COCF$_3$, R2=Cl, R3=R4=H, R5=CH$_3$O)

a. 2-[(5-chloro-2-fluorophenyl)iminomethyl]-3-methoxyphenol

Preparation analogous to Example 1, step a, from 5-chloro-2-difluoroaniline (9.57 g, 65.72 mmol) and 2-hydroxy-6-methoxybenzaldehyde (10 g, 65.72 mmol) gave the title compound (18.38 g, 100%). Data: $^1$H-NMR (400 MHz, CDCl$_3$) δ 3.89 (s, 3H), 6.38 (d, J=7.9 Hz, 1H), 6.61 (d, J=7.9 Hz, 1H), 7.07-7.36 (m, 4H), 9.16 (s, 1H), 13.68 (s, 1H).

b. 8-chloro-1-methoxydibenz[b,f][1,4]oxazepine

Preparation analogous to Example 8, step b, from 2-[(5-chloro-2-fluorophenyl)iminomethyl]-3-methoxyphenol (18.38 g, 65.72 mmol) gave the title compound (16.8 g, 98%). Data: $^1$H-NMR (400 MHz, CDCl$_3$) δ 3.88 (s, 3H), 6.73 (m, 2H), 7.02 (d, J=8.2 Hz, 1H), 7.15 (dd, J=8.2 Hz and 2.7 Hz, 1H), 7.32 (d, J=2.7 Hz, 1H), 7.39 (t, J=8.2 Hz, 1H), 8.79 (s, 1H).

c. 7-chloro-14b-dihydro-14-methoxy-2H-dibenzo[b,f]pyrido[1,2-d][1,4]oxazepin-2-one Preparation analogous to Example 1, step c, from the product of the previous step (16.8 g, 64.7 mmol) gave the crude compound which was crystallized from toluene/heptane to give 7-chloro-1,14b-dihydro-14-methoxy-2H-dibenzo[b,f]pyrido[1,2-d][1,4]oxazepin-2-one (13 g, 61%). $^1$H-NMR (400 MHz, CDCl$_3$) δ 2.75 (m, 1H), 2.89 (m, 1H), 3.8 (s, 3H), 5.39 (m, 1H), 5.48 (dd, J=12.7 Hz and 4.2 Hz, 1H), 6.70 (m, 1H), 6.90 (m, 1H), 7.10 (m, 1H), 7.16-7.24 (m, 2H), 7.44 (d, J=7.7 Hz, 1H).

d. (±)-trans-7-chloro-1,3,4,14b-dihydro-14-methoxy-2H-dibenzo[b,f]pyrido[1,2-d][1,4]oxazepin-2-ol Preparation analogous to Example 1, step d, from the product of the previous step (14 g, 43 mmol) gave the title compound (14.2 g, 99%). Data: $^1$H-NMR (400 MHz, CDCl$_3$) δ 1.74 (m, 1H), 1.88 (m, 1H), 2.12 (m, 1H), 2.27 (m, 1H), 3.13 (dt, J=11.6 Hz and 2.3, 1H), 3.59 (m, 1H), 3.79 (s, 3H), 3.93 (m, 1H), 4.3 (dd, J=10.8 Hz and 1.5 Hz, 1H), 6.64 (m, 1H), 6.76 (dd, J=8.2 Hz and 1.9 Hz, 1H), 6.86 (m, 1H), 7.01 (d, J=7.7 Hz, 1H), 7.13 (t, J=7.7 Hz, 1H).

e. (±)-cis-2-azido-7-chloro-1,3,4,14b-dihydro-14-methoxy-2H-dibenzo[b,f]pyrido[1,2-d][1,4]oxazepine Preparation analogous to Example 1, step g, from the alcohol obtained in the previous step (14.2 g, 43 mmol) gave the title compound (13.8 g, 90%). Data: $^1$H-NMR (400 MHz, CDCl$_3$) δ 1.82 (m, 1H), 2.01 (m, 1H), 2.10-2.26 (m, 2H), 3.28-3.43 (m, 2H), 3.80 (s, 1H), 4.12 (m, 1H), 4.65 (m, 1H), 6.63 (m, 1H), 6.77 (m, 1H), 6.85 (m, 1H), 6.94 (m, 1H), 7.00 (d, J=8.2 Hz, 1H), 7.1 (m, 1H).

f. (±)-cis-7-chloro-1,3,4,14b-dihydro-14-methoxy-2H-dibenzo[b,f]pyrido[1,2-d][1,4]oxazepine-2-amine Preparation analogous to Example 4, step f, from (±)-cis-2-azido-7-chloro-1,3,4,14b-dihydro-14-methoxy-2H-dibenzo[b,f]pyrido[1,2-d][1,4]oxazepine (13.8 g, 38.7 mmol) gave the crude title compound (11 g, 86%).

g. (±)-cis—N—[7-chloro-1,3,4,14b-dihydro-14-methoxy-2H-dibenzo[b,f]pyrido[1,2-d][1,4]oxazepin-2-yl]-2,2,2-trifluoroacetamide Preparation analogous to Example 1, step i, from the amine obtained in the previous step (11 g, 33.3 mmol) gave the title compound (4.6 g, 32%). Data: $^1$H-NMR (400 MHz, CDCl$_3$) δ 2.04-2.25 (m, 4H), 3.22 (dt, 11.6 Hz and 2.3, 1H), 3.47 (m, 1H), 3.77 (s, 3H), 4.30-4.34.38 (m, 2H), 6.60 (br, 1H), 6.64 (m, 1H), 6.81 (dd, J=8.2 Hz and 2.3 Hz, 1H), 6.88 (m, 1H), 6.93 (d, J=2.3 Hz, 1H), 7.03 (d, J=8.2 Hz, 1H), 7.16 (t, J=8.0 Hz, 1H). (m/z)=427+429 (M+H)$^+$.

Example 11

Preparation of (±)-cis—N—[8-bromo-7-chloro-1,3,4,14b-dihydro-14-methoxy-2H-dibenzo[b,f]pyrido[1,2-d][1,4]oxazepin-2-yl]-2,2,2-trifluoroacetamide (Formula I, X=O, R1=COCF$_3$, R2=Cl, R3=Br, R4=H, R5=CH$_3$O)

Preparation analogous to Example 4, step h, from the product obtained in the previous step (4.6 g, 10.8 mmol) gave the title compound (5.4 g, 99%). Data: (m/z)=505+507+509 (M+H)$^+$.

Example 12

Preparation of (±)-cis—N—[7-chloro-8-cyano-1,3,4,14b-dihydro-14-methoxy-2H-dibenzo[b,f]oxazepin[1,2-d][1,4]oxazepin-2-yl]-2,2,2-trifluoroacetamide (Formula I, X=O, R1=COCF$_3$, R2=Cl, R3=CN, R4=H, R5=CH$_3$O)

Preparation analogous to Example 2, from (±)-cis—N—[8-bromo-7-chloro-1,3,4,14b-dihydro-14-methoxy-2H-dibenzo[b,f]pyrido[1,2-d][1,4]oxazepin-2-yl]-2,2,2-trifluoroacetamide (5.4 g, 10.69 mmol) gave the title compound (2.87 g, 59%). Data: $^1$H-NMR (400 MHz, CDCl$_3$) δ 2.03-2.21 (m, 3H), 2.35 (m, 1H), 3.35 (dt, J=11.6 Hz and 3.8 Hz, 1H), 3.60 (m, 1H), 3.80 (s, 3H), 4.37 (m, 1H), 4.64 (m, 1H), 6.57 (br, 1H), 6.70 (m, 1H), 6.87 (m, 1H), 6.95 (s, 1H), 7.22 (t, J=7.7 Hz, 1H), 7.35 (m, 1H). (m/z)=452 (M+H)$^+$.

Example 13

Preparation of (±)-cis—N—[1,3,4,14b-dihydro-14-methoxy-2H-dibenzo b,f]pyrido[1,2-d][1,4]oxazepin-2-yl]-2,2,2-trifluoroacetamide (Formula I, X=O, R1=COCF$_3$, R2=H, R3=H, R4=H, R5=OCH$_3$)

a. 2-[[(2-fluoro-6-methoxyphenyl)methylene]amino]phenol

Preparation analogous to Example 1, step a, from 2-aminophenol (7.08 g, 64.93 mmol) and 2-fluoro-6-methoxybenzaldehyde (10 g, 64.93 mmol) gave the title compound (15.9 g, 99%).

b. 1-methoxydibenz[b,f][1,4]oxazepine

Preparation analogous to Example 1, step b, from the phenol obtained in the previous step (15.9 g, 113 mmol) gave the title compound (3.4 g, 23%). Data: $^1$H-NMR (400 MHz, CDCl$_3$) δ 3.87 (s, 3H), 6.70 (d, J=8.2 Hz, 1H), 6.76 (d, J=8.1 Hz, 1H), 7.10 (m, 1H), 7.19 (m, 2H), 7.32-7.40, 8.80 (s, 1H). (m, 2H). (m/z)=244 (M+H)$^+$.

c. 1,14b-dihydro-14-methoxy-2H-dibenzo[b,f]pyrido[1,2-d][1,4]oxazepin-2-one

Preparation analogous to Example 1, step c, from 1-methoxydibenz[b,f][1,4]oxazepine (3.4 g, 15.11 mmol) gave the crude title compound (3.2 g, 72%). Data: $^1$H-NMR (400 MHz, CDCl$_3$) δ 2.75 (m, 1H), 2.90 (m, 1H), 3.80 (s, 3H), 5.36 (m, 1H), 5.48 (dd, J=13.5 Hz and 3.8 Hz, 1H), 6.69 (d, J=8.5 Hz, 1H), 6.93 (d, J=8.5 Hz, 1H), 7.12-7.27 (m, 4H), 7.49 (d, J=8.5 Hz, 1H). (m/z)=294 (M+H)$^+$.

d. (±)-trans-1,3,4,14b-dihydro-14-methoxy-2H-dibenzo[b,f]pyrido[1,2-d][1,4]oxazepin-2-ol Preparation analogous to Example 1, step d, from the compound obtained in the previous step (3.2 g, 10.92 mmol) gave the title compound (14.24 g, 100%). Data: $^1$H-NMR (400 MHz, CDCl$_3$) δ 1.75 (m, 1H), 1.84 (m, 1H), 2.10 (m, 1H), 2.30 (m, 1H), 3.13 (dt, J=11.6 Hz and 2.3 Hz, 1H), 3.59 (m, 1H), 3.77 (s, 3H), 3.90 (m, 1H), 4.26 (m, 1H), 6.60 (m, 1H), 6.80 (m, 1H), 6.68 (m, 1H), 6.97 (m, 1H), 7.00-7.25 (m, 3H).

e. (±)-cis-2-azido-1,3,4,14b-dihydro-14-methoxy-2H-dibenzo[b,f]pyrido[1,2-d][1,4]oxazepine Preparation analogous to Example 1, step g, from (±)-trans-1,3,4,14b-dihydro-14-methoxy-2H-dibenzo[b,f]pyrido[1,2-d][1,4]oxazepin-2-ol (3.2 g, 10.77 mmol) gave the title compound (2.32 g, 67%). Data: $^1$H-NMR (400 MHz, CDCl$_3$) δ 1.83 (m, 1H), 2.07 (m, 1H), 2.16 (m, 1H), 2.28 (m, 1H), 3.32-3.46 (m, 2H), 3.80 (s, 3H), 4.13 (m, 1H), 4.62 (m, 1H), 6.62 (d, J=8.2 Hz, 1H), 6.85 (m, 2H), 7.00 (m, 1H), 7.05. 7.20 (m, 3H). (m/z)=323 (M+H)$^+$.

f. (±)-cis-1,3,4,14b-dihydro-14-methoxy-2H-dibenzo[b,f]pyrido[1,2-d][1,4]oxazepine-2-amine Preparation analogous to Example 1, step h, from the azide obtained in the previous step (2.12 g, 6.6 mmol) gave the title compound (1.89 g, 97%). Data: (m/z)=297 (M+H)$^+$.

g. (±)-cis—N—[1,3,4,14b-dihydro-14-methoxy-2H-dibenzo[b,f]pyrido[1,2-d][1,4]oxazepin-2-yl]-2,2,2-trifluoroacetamide Preparation analogous to Example 1, step i, from the amine obtained in the previous step (1.89 g, 6.38 mmol) to afford the crude compound which was purified by flash chromatography (SiO$_2$, CH$_2$Cl$_2$) to give the title compound (2.03 g, 81%). Data: $^1$H-NMR (400 MHz, CDCl$_3$) δ 2.03-2.26 (m, 4H), 3.23 (dt, J=11.6 Hz and 2.7 Hz, 1H), 3.47 (m, 1H), 3.75 (s, 3H), 4.32 (m, 2H), 6.61 (m, 1H), 6.64 (br, 1H), 6.87 (m, 2H), 6.97 (m, 1H), 7.06-7.20 (m, 3H). (m/z)=393 (M+H)$^+$.

Example 14

Preparation of (±)-cis—N—[1,3,4,14b-dihydro-14-methyl-2H-dibenzo[b,f]pyrido[1,2-d][1,4]oxazepin-2-yl]-2,2,2-trifluoroacetamide (Formula I, X=O, R1=COCF$_3$, R2=H, R3=R4=H, R5=CH$_3$)

a. (±)-cis—N—[1,3,4,14b-dihydro-14-hydroxy-dibenzo[b,f]pyrido[1,2-d][1,4]oxazepin-2-yl]-2,2,2-trifluoroacetamide (±)-cis—N—[1,3,4,14b-dihydro-14-methoxy-2H-dibenzo[b,f]pyrido[1,2-d][1,4]oxazepin-2-yl]-2,2,2-trifluoroacetamide (2.03 g, 5.17 mmol) in a mixture of CH$_2$Cl$_2$ (75 mL) and boron trifluoride-methyl sulfide complex (8.5 mL, 83.2 mmol) was stirred at ambient temperature for 2 h. The reaction mixture was then poured into saturated (aq) NaHCO$_3$ solution, the organic layer was separated, washed with brine, dried (Na$_2$SO$_4$) and concentrated to afford the crude compound which was purified by flash chromatography (SiO$_2$, toluene) to give the title compound (1.45 g, 74%). Data: $^1$H-NMR (400 MHz, CDCl$_3$) δ 2.04-2.32 (m, 4H), 3.23 (dt, J=11.6 Hz and 2.7 Hz, 1H), 3.47 (m, 1H), 4.33 (m, 2H), 5.24 (br, 1H), 6.46 (m, 1H), 6.66 (br, 1H), 6.84-7.14 (m, 6H). (m/z)=379 (M+H)$^+$.

b. (±)-cis-[7-chloro-1,3,4,14b-dihydro-2-[(trifluoroacetyl)amino]-2H-dibenzo[b,f]pyrido[1,2-d][1,4]oxazepin-14-yl]trifluoromethylsulfonate To a mixture of the product obtained in the previous step (1.45 g, 3.83 mmol) and triethylamine (0.6 mL, 4.2 mmol) in CH$_2$Cl$_2$ (70 mL) at −70° C. was added triflic anhydride (0.73 mL, 4.3 mmol) dropwise and stirred at −70° C. for 1 h. The reaction mixture was poured into water and extracted with CH$_2$Cl$_2$. The organic layer was washed with brine, dried (Na$_2$SO$_4$) and concentrated to afford the crude title compound (1.95 g, 100%) which was used without further purification. Data: $^1$H-NMR (400 MHz, CDCl$_3$) δ 2.09 (m, 3H), 2.52 (m, 1H), 3.32 (m, 1H), 3.60 (m, 1H), 4.40 (m, 1H), 4.44 (m, 1H), 6.86 (br, 1H), 6.89 (m, 1H) 6.99-7.33 (m, 6H). (m/z)=511 (M+H)$^+$.

c. (±)-cis—N—[1,3,4,14b-dihydro-14-methyl-2H-dibenzo[b,f]pyrido[1,2-d][1,4]oxazepin-2-yl]-2,2,2-trifluoroacetamide A mixture of the sulfonate obtained in the previous step (1.95 g, 3.83 mmol), 1,1'-bis(diphenylphosphino)ferrocene dichloropalladium(II) (16 mg, 0.02 mmol) and 2M methylzinc chloride in THF (3.83 mL, 7.66 mmol) in THF (60 mL) was stirred at 60° C. for 1.5 h. After cooling down, the reaction mixture was poured into saturated (aq) NH$_4$Cl solution the organic layer was washed with brine, dried (Na$_2$SO$_4$) and evaporated to afford the crude compound which was purified by flash chromatography (SiO$_2$, CH$_2$Cl$_2$) to give (±)-cis—N—[1,3,4,14b-dihydro-14-methyl-2H-dibenzo[b,f]pyrido[1,2-d][1,4]oxazepin-2-yl]-2,2,2-trifluoroacetamide (1.3 g, 90%). Data: $^1$H-NMR (400 MHz, CDCl$_3$) δ 1.91 (m, 1H), 2.09 (m, 1H), 2.19 (s, 3H), 2.31 (m, 2H), 3.30 (d, J=11.6 Hz and 2.3 Hz, 1H), 3.63 (m, 1H), 4.24 (dd, J=11.2 Hz and 1.5 Hz, 1H), 4.41 (m, 1H), 6.58 (br, 1H), 6.81-7.14 (m, 7H), (m/z)=377 (M+H)$^+$.

Example 15

Preparation of (±)-cis—N—[8-bromo-1,3,4,14b-dihydro-14-methyl-2H-dibenzo[b,f]pyrido[1,2-d][1,4]oxazepin-2-yl]-2,2,2-trifluoroacetamide (Formula I, X=O, R1=COCF$_3$, R2=H, R3=Br, R4=H, R5=CH$_3$)

Preparation analogous to Example 5, from (±)-cis—N—[1,3,4,14b-dihydro-14-methyl-2H-dibenzo[b,f]pyrido[1,2-d][1,4]oxazepin-2-yl]-2,2,2-trifluoroacetamide (1.3 g, 3.45 mmol) produced the title compound (1.55 g, 98%). Data: $^1$H-NMR (400 MHz, CDCl$_3$) δ 1.90 (m, 1H), 2.08 (m, 1H), 2.20 (s, 3H), 2.21-2.38 (m, 2H), 3.30 (m, 1H), 3.58 (m, 1H), 4.26 (m, 1H), 4.41 (m, 1H), 6.55 (br, 1H), 6.81 (d, J=8.2 Hz, 1H), 6.93 (m, 1H), 7.07-7.27 (m, 4H). (m/z)=455+457 (M+H)$^+$.

Example 16

Preparation of (±)-cis—N—[8-cyano-1,3,4,14b-dihydro-14-methyl-2H-dibenzo[b,f]pyrido[1,2-d][1,4]oxazepin-2-yl]-2,2,2-trifluoroacetamide (Formula I, X=O, R1=COCF$_3$, R2=H, R3=CN, R4=H, R5=CH$_3$)

Preparation analogous to Example 2, from the compound obtained in the previous step (1.55 g, 3.4 mmol) gave the title compound (1.0 g, 73%). Data: $^1$H-NMR (400 MHz, CDCl$_3$) δ 1.91 (m, 1H), 2.04 (m, 1H), 2.22 (m, 1H), 2.24 (s, 3H), 2.53 (m, 1H), 3.45 (m, 1H), 3.80 (m, 1H), 4.43 (m, 1H), 4.48 (m, 1H), 6.59 (br, 1H), 6.90 (d, J=8.2 Hz, 1H), 6.98 (m, 1H), 7.07-7.39 (m, 4H).

Example 17

Preparation of methyl(±)-cis—N—[8-cyano-1,3,4,14b-dihydro-14-methyl-2H-dibenzo[b,f]pyrido[1,2-d]1,4]oxazepin-2-yl]carbamate (Formula I, X=O, R1=COOCH$_3$, R2=H, R3=CN, R4=H, R5=CH$_3$)

a. (±)-cis-2-amino-1,3,4,14b-dihydro-14-methyl-2H-dibenzo[b,f]pyrido[1,2-d][1,4]oxazepine-8-carbonitrile Preparation analogous to Example 3, step a, from the compound obtained from Example 16 (1.0 g, 2.49 mmol) gave the title compound (0.685 g, 90%). Data: $^1$H-NMR (400 MHz, CDCl$_3$) δ 1.54 (m, 2H), 2.02 (m, 1H), 2.36 (s, 3H), 2.57 (m, 1H), 3.64 (m, 2H), 3.76 (m, 1H), 5.02 (m, 1H), 6.89 (d, J=8.2 Hz, 1H), 6.98 (m, 1H), 7.03-7.35 (m, 4H). Data: (m/z)=306 (M+H)$^+$.

b. methyl(±)-cis—N—[8-cyano-1,3,4,14b-dihydro-14-methyl-2H-dibenzo[b,f]pyrido[1,2-d][1,4]oxazepin-2-yl]carbamate Preparation analogous to Example 2, from the product obtained in the previous step (50 mg, 0.164 mmol) and methyl chloroformate (18.46 mg, 0.197). The crude compound was purified by HPLC to give the title carbamate (40 mg, 67%). Data: $^1$H-NMR (400 MHz, CDCl$_3$) δ 1.83 (m, 1H), 1.95 (m, 1H), 2.10 (m, 1H), 2.27 (s, 3H), 2.47 (m, 1H), 3.42 (dt, J=11.6 Hz and 2.3 Hz, 1H), 36.3 (m, 4H), 4.14 (m, 1H), 4.44 (dd, J=11.6 Hz and 1.5 Hz, 1H), 5.00 (br, 1H), 6.89 (d, J=7.7 Hz, 1H), 6.96 (d, J=7.7 Hz, 1H), 7.10 (m, 2H), 7.30 (dd, J=8.6 Hz and 1.5 Hz, 1H), 7.35 (d, J=1.5 Hz, 1H). MIM=363.

Example 18

Preparation of (±)-cis—N—[8-cyano-1,3,4,14b-dihydro-14-methyl-2H-dibenzo[b,f]pyrido[1,2-d][1,4]oxazepin-2-yl]acetamide (Formula I, X=O, R1=COCH$_3$, R2=H, R3=CN, R4=H, R5=CH$_3$)

Preparation analogous to Example 3, step b, from the compound obtained in Example 17, step a (50 mg, 0.164 mmol). The crude compound was purified by HPLC to give the title compound (26 mg, 45%). Data: $^1$H-NMR (400 MHz, CDCl$_3$) δ 1.81 (m, 1H) 2.00 (m, 1H), 2.10 (s, 3H), 2.14 (m, 1H), 2.26 (s, 3H), 2.44 (m, 1H), 3.42 (dd, J=12.4 Hz and 2.7 Hz, 1H), 3.63 (m, 1H), 2.36 (m, 1H), 4.50 (dd, J=11.6 Hz and 2.0 Hz, 1H), 5.79 (br, 1H), 6.88 (d, J=8.5 Hz, 1H), 6.96 (m, 1H), 7.11 (m, 2H), 7.3 (dd, J=8.5 Hz and 1.5 Hz, 1H), 7.35 (d, J=1.5 Hz, 1H). (m/z)=348 (M+H)+.

Example 19

Preparation of (±)-cis—N—[8-cyano-1,3,4,14b-dihydro-14-methyl-2H-dibenzo[b,f]pyrido[1,2-d][1,4]oxazepin-2-yl]sulfonamide (Formula I, X=O, R1=SO$_2$CH$_3$, R2=H, R3=CN, R4=H, R5=CH$_3$)

Preparation analogous to Example 3, step b, from the compound obtained in Example 17, step a (50 mg, 0.164 mmol) and mesyl chloride (23.68 mg, 0.197). The crude compound was purified by HPLC to give the title sulfonamide (41 mg, 65%). Data: $^1$H-NMR (400 MHz, CDCl$_3$) δ 1.86 (m, 1H), 1.96 (m, 1H), 2.17 (m, 1H), 2.36 (s, 3H), 2.60 (m, 1H), 3.05 (s, 3H), 3.51 (dt, J=12.0 Hz and 2.3 Hz, 1H), 3.77 (m, 1H), 4.01 (m, 1H), 4.68 (dd, J=12.0 Hz and 1.5 Hz, 1H), 4.75 (d, J=5.0 Hz, 1H), 6.89 (d, 8.0, 1H), 6.99 (d, J=8.0. 1H), 7.07 (m, 1H), 7.14 (t, J=7.7 Hz, 1H), 7.30 (dd, J=8.5 Hz and 1.5 Hz, 1H), 7.35 (d, J=1.5 Hz, 1H). MIM=383.

Example 20

Preparation of (±)-cis—N—[8-cyano-1,3,4,14b-dihydro-14-methyl-2H-dibenzo[b,f]pyrido[1,2-d][1,4]oxazepin-2-yl]-2-propynamide (Formula I, X=O, R1=COC$_2$H, R2=H, R3=CN, R4=H, R5=CH$_3$)

A mixture of (±)-cis-2-amino-1,3,4,14b-dihydro-14-methyl-2H-dibenzo[b,f]pyrido[1,2-d][1,4]oxazepine-8-carbonitrile (65 g, 0.213 mmol), DIPEA (139 mg, 1.07 mmol), TBTU (103 mg, 0.32 mmol) and propiolic acid (22.6 mg, 0.32 mmol) in CH$_2$Cl$_2$ was stirred at ambient temperature for 2 h. The reaction mixture was poured into saturated (aq) NaHCO$_3$ solution, the organic layer was separated, washed with brine, dried (Na$_2$SO$_4$) and concentrated to afford the crude compound which was purified by HPLC to give the title amide (29 mg, 38%). Data: $^1$H-NMR (400 MHz, CDCl$_3$) δ 1.86 (m, 1H), 2.02 (m, 1H), 2.16 (m, 1H), 2.29 (s, 3H), 2.47 (m, 1H), 2.86 (s, 1H), 3.45 (dd, J=11.6 Hz and 2.3 Hz, 1H), 3.76 (m, 1H), 4.42 (m, 1H), 4.52 (m, 1H), 6.16 (br, 1H), 6.89 (d, J=7.7 Hz, 1H), 6.97 (d, J=7.7 Hz, 1H), 7.13 (m, 2H), 7.31 (m, 1H), 7.36 (d, J=1.5 Hz, 1H). (m/z)=357 (M+H)+.

Example 21

Preparation of (±)-cis—N—[7-chloro-1,3,4,14b-dihydro-14-methyl-2H-dibenzo[b,f]pyrido[1,2-d][1,4]oxazepin-2-yl]-2,2,2-trifluoroacetamide (Formula I, X=O, R1=COCF$_3$, R2=Cl, R3=H, R4=H, R5=CH$_3$)

a. (±)-cis—N—[7-chloro-1,3,4,14b-dihydro-14-hydroxy-2H-dibenzo[b,f]pyrido[1,2-d][1,4]oxazepin-2-yl]-2,2,2-trifluoroacetamide Preparation analogous to Example 14, step a, from the product obtained from Example 10, step g (0.65 g, 1.52 mmol), to afford the crude title compound (0.627 g, 100%) which was used without further purification. Data: $^1$H-NMR (400 MHz, CDCl$_3$) δ 2.07-2.29 (m, 4H), 3.23 (dt, J=3 Hz and 13 Hz, 1H), 3.43-3.49 (m, 1H), 4.32-4.39 (m, 2H), 5.22 (s, 1H), 6.47-6.51 (m, 1H), 6.64 (brs, 1H), 6.81-6.86 (m, 2H), 6.95 (d, J=2 Hz, 1H), 6.99-7.06 (m, 2H).

b. (±)-cis-[7-chloro-1,3,4,14b-dihydro-2-[(trifluoroacetyl)amino]-2H-dibenzo[b,f]pyrido[1,2-d][1,4]oxazepin-14-yl]trifluoromethylsulfonate Preparation analogous to Example 14, step b, from the product obtained in the previous step (0.627 g, 1.52 mmol) to afford the crude compound which was purified by flash chromatography (SiO$_2$, heptane/ethyl acetate) to give (±)-cis-[7-chloro-1,3,4,14b-dihydro-2-[(trifluoroacetyl)amino]-2H-dibenzo[b,f]pyrido[1,2-d][1,4]oxazepin-14-yl]trifluoromethylsulfonate (0.828 g, 100%). Data: $^1$H-NMR (400 MHz, CDCl$_3$) δ 2.02-2.12 (m, 3H), 2.49-2.58 (m, 1H), 3.29-3.37 (m, 1H), 3.56-3.64 (m, 1H), 4.35-4.42 (m, 1H), 4.44-4.50 (m, 1H), 6.81-6.87 (m, 2H), 6.96-7.07 (m, 2H), 7.24-7.35 (m, 2H).

c. (±)-cis—N—[7-chloro-1,3,4,14b-dihydro-14-methyl-2H-dibenzo[b,f]pyrido[1,2-d][1,4]oxazepin-2-yl]-2,2,2-trifluoroacetamide Preparation analogous to Example 14, step c, from the sulfonate obtained in the previous step (0.917 g, 1.68 mmol) to afford the crude compound which was purified by flash chromatography (SiO$_2$, heptane/ethyl acetate) to give the title compound (0.604 g, 88%). Data: $^1$H-NMR (400 MHz, CDCl$_3$) δ 1.87-1.94 (m, 1H), 2.05-2.11 (m, 1H), 2.19 (s, 3H), 2.21-2.39 (m, 2H), 3.31 (dt, J=3 Hz and 13 Hz, 1H), 3.58-3.64 (m, 1H), 4.28 (dd, J=2 Hz and 12 Hz, 1H), 4.41 (brs 1H), 6,78 (dd, J=2 Hz and 9 Hz, 1H), 6.89-6.94 (m, 2H), 7.02 (d, J=9 Hz, 1H), 7.06-7.10 (m, 2H).

Example 22

Preparation of (±)-cis—N—[8-bromo-7-chloro-1,3,4,14b-dihydro-14-methyl-2H-dibenzo[b,f]pyrido[1,2-d][1,4]oxazepin-2-yl]-2,2,2-trifluoroacetamide (Formula I, X=O, R1=COCF$_3$, R2=Cl, R3=Br, R4=H, R5=CH$_3$)

Preparation analogous to Example 5, from the product obtained in example 21, step c (0.604 g, 1.47 mmol) gave the title compound (±)-cis—N—[8-bromo-7-chloro-1,3,4,14b-dihydro-14-methyl-2H-dibenzo[b,f]pyrido[1,2-d][1,4]oxazepin-2-yl]-2,2,2-trifluoroacetamide (0.718 g, 99%). Data: $^1$H-NMR (400 MHz, CDCl$_3$) δ 1.87-1.95 (m, 1H), 2.04-2.11 (m, 1H), 2.20 (s, 3H), 2.19-2.40 (m, 2H), 3.32 (dt, J=3 Hz and 13 Hz, 1H), 3.56-3.64 (m, 1H), 4.29 (dd, J=2 Hz and 12 Hz, 1H), 4.41 (brs 1H), 6.54 (brs 1H), 6.92-6.96 (m, 1H), 7.00 (s, 1H), 7.05-7.13 (m, 2H), 7.37 (s, 1H).

Example 23

Preparation of (±)-cis—N—[7-chloro-8-nitro-1,3,4,14b-dihydro-14-methyl-2H-dibenzo[b,f]pyrido[1,2-d][1,4]oxazepin-2-yl]-2,2,2-trifluoroacetamide ORG 216187-0, HS2046

(Formula I, X=O, R1=COCF$_3$, R2=Cl, R3=NO$_2$, R4=H, R5=CH$_3$)

A solution of (±)-cis—N—[7-chloro-1,3,4,14b-dihydro-14-methyl-2H-dibenzo[b,f]pyrido[1,2-d][1,4]oxazepin-2-yl]-2,2,2-trifluoroacetamide (45 mg, 0.11 mmol) in acetic anhydride (0.7 mL) was added to a stirred solution of nitric acid (7.5 μL, 0.17 mmol) in acetic anhydride (0.7 mL) at −60°

C. and the reaction mixture stirred for 1 h at −20° C. and for 2 h at 0° C. Saturated (aq) NaHCO₃ solution was added, and the mixture extracted with ethyl acetate. The organic layer was washed with brine, dried (Na₂SO₄) and concentrated to afford the crude compound which was purified by HPLC to give the title product (17 mg, 34%). Data: ¹H-NMR (400 MHz, CDCl₃) δ 1.90-1.97 (m, 1H), 2.23-2.29 (m, 1H), 2.17-2.28 (m, 1H), 2.25 (s, 3H), 2.55-2.64, (m, 1H), 3.52 (dt, J=3 Hz and 13 Hz, 1H), 3.84-3.91 (m, 1H), 4.44 (brs 1H), 4.56 (dd, J=2 Hz and 12 Hz, 1H), 6.49 (brs 1H), 6.92 (s, 1H), 6.98-7.25 (m, 3H), 7.90 (s, 1H).

Example 24

Preparation of (±)—N—[(cis)-1,3,4,14b-tetrahydro-2H-dibenzo[b,f]pyrido[1,2-d][1,4]oxazepin-2-yl]-2,2,2-trifluoroacetamide (Formula I, X=O, R1=COCF₃, R2=H, R3=H, R4=H, R5=H)

Preparation analogous to Example 1, step i, from 2.9 g (10.9 mmol) of crude (±)—N—(cis)-1,3,4,14b-tetrahydro-2H-dibenzo[b,f]pyrido[1,2-d][1,4]oxazepine-2-amine (W. J. van der Burg, U.S. Pat. No. 4,016,161) gave, after chromatography (heptane/ethyl acetate), the title amide (2.2 g, 56%). Data: ¹H-NMR (400 MHz, CDCl₃) δ 1.90 (m, 1H), 2.05 (m, 1H), 2.18 (m, 1H), 2.51 (m, 1H), 3.20-3.37 (m, 2H), 4.50 (m, 1H), 4.80 (m, 1H), 6.39 (bs, 1H), 6.86-7.31 (m, 8 Ar—H). (m/z)=363 (M+H)⁺.

Example 25

Preparation of (±)—N—[(cis)-8-bromo-1,3,4,14b-tetrahydro-2H-dibenzo[b,f]pyrido[1,2-d][1,4]oxazepin-2-yl]-2,2,2-trifluoroacetamide (Formula I, X=O, R1=COCF₃, R2=H, R3=Br, R4=H, R5=H)

Preparation analogous to Example 5 from 1.0 g (2.76 mmol) of the compound of example 24, gave the title compound (1.22 g, 100%). Data: ¹H-NMR (400 MHz, DMSO) δ 1.90 (m, 2H), 1.97 (m, 1H), 2.25 (m, 1H), 3.02 (m, 1H), 3.38 (m, 1H), 4.27 (m, 1H), 4.86 (m, 1H), 7.05 (d, 1 Ar—H), 7.16-7.32 (m, 5 Ar—H), 7.39 (dd, 1 Ar—H), 9.53 (bd, 1H). (m/z)=442 (M+H)⁺.

Example 26

Preparation of (±)—N—[(cis)-8-cyano-1,3,4,14b-tetrahydro-2H-dibenzo[b,f]pyrido[1,2-d][1,4]oxazepin-2-yl]-2,2,2-trifluoroacetamide ORG 51526-0 MOMA 0297A (Formula I, X-=O, R1=COCF₃, R2=H, R3=CN, R4=H, R5=H)

Preparation analogous to Example 2, from 200 mg (0.454 mmol) of the compound of example 25, gave the title compound (176 mg, 100%). Data: ¹H-NMR (400 MHz, DMSO) δ 1.80-1.97 (m, 3H), 2.40 (m, 1H), 3.26 (m, 1H), 3.55 (m, 1H), 4.30 (m, 1H), 5.06 (m, 1H), 7.19-7.36 (m, 4 Ar—H), 7.42 (m, 2 Ar—H), 7.58 (d, 1 Ar—H), 9.58 (bd, 1H). (m/z) =388 (M+H)⁺.

Example 27

Preparation of (±)—N—[(cis)-8-(aminothioxomethyl)-1,3,4,14b-tetrahydro-2H-dibenzo[b,f]pyrido[1,2-d][1,4]oxazepin-2-yl]-2,2,2-trifluorothioacetamide (Formula I, X=O, R1=CSCF₃, R2=H, R3=CSNH2, R4=H, R5=H)

To a solution of (±)—N—[(cis)-8-cyano-1,3,4,14b-tetrahydro-14-methyl-2H-dibenzo[b,f]pyrido[1,2-d][1,4]oxazepin-2-yl]-2,2,2-trifluoroacetamide (176 mg, 0.454 mmol) in dioxane (12 mL) was added phosphorus pentasulfide (2.62 mg, 0.590 mmol), and the resulting mixture stirred at 60° C. for 3 h. The reaction mixture was diluted with ethyl acetate, poured into water, and extracted with ethyl acetate. The combined organic layers were washed with brine, dried (Na₂SO₄) and evaporated to afford the crude compound which was purified by prep-HPLC(CH₃CN/H₂O) to give (±)—N—[(cis)-8-(aminothioxomethyl)-1,3,4,14b-tetrahydro-14-methyl-2H-dibenzo[b,f]pyrido[1,2-d][1,4]oxazepin-2-yl]-2,2,2-trifluorothioacetamide (52 mg, 25%). Data: ¹H-NMR (400 MHz, DMSO) δ 1.94-2.15 (m, 3H), 2.47 (m, 1H), 3.20 (m, 1H), 3.57 (m, 1H), 4.90 (m, 1H), 5.24 (m, 1H), 7.10 (d, 1 Ar—H), 7.20-7.26 (m, 2 Ar—H), 7.34 (m, 1 Ar—H), 7.65 (m, 2 Ar—H) 7.78 (d, 1 Ar—H). 9.30 (bs, 1H), 9.64 (bs, 1H), 11.30 (bs, 1H). (m/z)=438 (M+H)⁺.

Example 28

Preparation of (±)—N—[(cis)-1,3,4,14b-tetrahydro-13-methyl-2H-dibenzo[b,f]pyrido[1,2-d][1,4]thiazepin-2-yl]-2,2,2-trifluoroacetamide (Formula I, X=S, R1=COCF₃, R2=H, R3=H, R4=CH₃, R5=H)

Preparation analogous to Example 1, step i, starting from (±)-2-amino-13-methyl-1,3,4,14b-tetrahydro-2H-pyridino[1,2-d]dibenzo[b,f][1,4]thiazepine (W. J. van der Burg, U.S. Pat. No. 4,016,161). Treatment of the amine (0.20 mg, 0.68 mmol) with ethyl trifluoroacetate (1.25 g, 8.78 mmol) and triethylamine (0.35 g, 3.48 mmol) in methanol (10 mL) gave, after purification by HPLC, 0.13 g, (54%) of (±)—N—[(cis)-1,3,4,14b-tetrahydro-13-methyl-2H-dibenzo[b,f]pyrido[1,2-d][1,4]thiazepin-2-yl]-2,2,2-trifluoroacetamide. Data: ¹H-NMR (400 MHz, CDCl₃) δ 1.82-1.94 (m, 2H), 2.23 (m, 1H), 2.28 (s, 3H), 2.60 (m, 1H), 3.25 (m, 1H), 3.40 (m, 1H), 4.52 (m, 1H), 4.71 (m, 1H), 6.49 (br, 1H), 6.81 (m, 1H), 6.93 (m, 2H), 6.97 (m, 1H), 7.17 (m, 1H), 7.35-7.39 (m, 2H). (m/z)=393 (M+H)⁺.

Example 29

Preparation of (−)-cis—N—[8-cyano-7-fluoro-1,3,4,14b-dihydro-14-methyl-2H-dibenzo[b,f]pyrido[1,2-d[1,4]oxazepin-2-yl]-2,2,2-trifluoroacetamide (Formula I, X=O, R1=COCF₃, R2=F, R3=CN, R4=H, R5=CH₃)

The two enantiomers of Example 6 (199 mg, in portions of 20 mg) were separated with HPLC using chiral AD-H-column (2 cm Ø×25 cm) to yield the title enantiomer (53 mg, 26%). %). Data: e.e.=99.7%, $R_t$=9.7 min. (chiralpak AD-H 25*0.46 cm, heptane:isopropanol=8:2). ¹H-NMR (400 MHz, DMSO) δ 1.80 (m, 2H), 1.99 (m, 1H), 2.23 (s, 3H), 2.46 (m, 1H), 3.82 (m, 2H), 4.26 (m, 1H), 4.74 (m, 1H), 7.03-7.24 (m, 4H), 7.64 (d, J=6.5 Hz, 1H), 9.66 (br, 1H). MIM=419. $[\alpha]_D^{20}$=−496° (c=1.01, THF).

Example 30

Preparation of (−)-cis—N—[8-cyano-7-fluoro-1,3,4,14b-dihydro-14-methyl-2H-dibenzo[b,f]pyrido[1,2-d][1,4]oxazepin-2-yl]acetamide (Formula I, X=O, R1=COCH$_3$, R2=F, R3=CN, R4=H, R5=CH$_3$)

The two enantiomers of Example 7 (241 mg, in portions of 30 mg) were separated with HPLC using chiral AD-H-column (2 cm Ø×25 cm) and, as mobile phase (isocratic), a mixture of heptane/ethanol (85:15, v/v), to give the title enantiomer (53 mg, 22%). Data: e.e.=99.9%, R$_f$=9.4 min. (chiralpak AD-H 25*0.46 cm, heptane:ethanol=8:2). $^1$H-NMR (400 MHz, DMSO) δ 1.61 (m, 1H), 1.71 (m, 1H), 1.88 (m, 1H), 1.92 (s, 3H), 2.24 (s, 3H), 2.33 (m, 1H), 3.68 (m, 1H), 3.82 (m, 1H), 4.14 (m, 1H), 4.72 (m, 1H), 7.04-7.22 (m, 4H), 7.63 (d, J=7.0 Hz, 1H), 8.27 (d-br, J=7.0 Hz, 1H). MIM=365. $[\alpha]_D^{20}$=−608° (c=0.4, THF).

Example 31

Preparation of (−)-cis—N—[8-cyano-1,3,4,14b-dihydro-14-methoxy-2H-dibenzo[b,f]pyrido[1,2-d][1,4]oxazepin-2-yl]-2,2,2-trifluoroacetamide (Formula I, X=O, R1=COCF$_3$, R2=H, R3=CN, R4=H, R5=CH$_3$O)

The two enantiomers of the end product of Example 9 (205 mg, in portions of 35 mg) were separated with HPLC using a chiral AS-column (2 cm Ø×25 cm) and, as mobile phase (isocratic), a mixture of heptane/isopropanol/ethanol (80:15:5, v/v/v), to give the title enantiomer (74 mg, 36%). Mp 141-142° C. Data: e.e.=99.9%, R$_f$=8.4 min. (chiralpak AS 25*0.46 cm, heptane:ethanol=8:2). $^1$H-NMR (400 MHz, DMSO) δ 1.83 (m, 1H), 1.92-2.18 (m, 4H), 3.54 (m, 1H), 4.20 (m, 1H), 4.71 (m, 1H), 6.83 (d, J=8.1 Hz, 1H), 6.92 (d, J=8.1 Hz, 1H), 7.11 (d, J=8.5 Hz, 1H), 7.24 (t, J=8.1 Hz, 1H), 7.50 (dd, J=8.1 Hz and 2.0 Hz, 1H), 7.58 (d, J=2.0 Hz, 1H), 9.55 (br, 1H). MIM=417. $[\alpha]_D^{20}$=−568° (c=1.13, THF).

Example 32

Progesterone Receptor-B Activity and Glucocorticoid Activity in a Transactivation The progestagenic activity of a compound of the invention (EC$_{50}$ and intrinsic agonistic activity) was determined in an in vitro bioassay of Chinese hamster ovary (CHO) cells as described by W. G. E. J. Schoonen et al. (Anal. Biochem. 261 (1998), 222-224). To express the activity of a compound, the EC50 is often employed, the EC50 being the concentration of the compound being studied where the effect for a certain activity is half (50%) of the maximum effect that can be reached for said activity. Preferably, the EC50 is $10^{-7}$ or lower; more preferably, the EC50 is $10^{-8}$ or lower; most preferably, the EC50 is $10^{-9}$ or lower.

The glucocorticoid activity of a compound of the invention (EC50 and intrinsic activity) was determined in an in vitro bioassay of CHO cells stably transfected with the human glucocorticoid receptor expression plasmid and with a reporter plasmid in which the MMTV-promoter is linked to the luciferase reporter gene. The bioassay with the cell line, known under the name CHO-GR B4.8, is performed analogous to the bio-assay with the cell-line CHO-PRB-pMMTV-LUC 1E2-A2 as described in Dijkema et al. (1998) J. Steroid Biochem. Mol. Biol. 64:147-56. The cells were cultured with charcoal-treated supplemented defined bovine calf serum from Hyclone (Utah, USA) in Dulbecco's Modified Eagles Medium/Nutrient Mixture F-12 (DMEM/HAM F12 in ratio 1:1) from Gibco (Paisley, UK).

The selectivity of one activity over another activity for a compound can be determined by comparison of the difference of the two activities concerned. For such a comparison, the ratio of the two EC50s concerned is frequently employed. Preferably, the selectivity is a factor of ten (that is, the concentration at which the 50% level is reached for one activity is ten times higher than the concentration of the same compound at which the 50% level is reached for a second activity; in such a case, the compound is said to be selective for the latter activity) or higher; more preferably, the selectivity is a factor of one hundred or higher; most preferably, the selectivity is a factor of one thousand or higher.

The compounds of the subject invention showed selectivity in their activity towards the progesterone and glucocorticoid receptors. The activity of the compounds of the subject invention towards the progesterone receptor was considerably higher than the activity towards the glucocorticoid receptor; thus, as outlined in the definition given before, the concentration of a compound of the subject invention at which a progestagenic effect is produced is much lower than the concentration at which the same compound produces a glucocorticoid effect.

The invention claimed is:

1. A (cis)-dibenzo[bf]pyrido[1,2-d]oxazepine-2-amine or a (cis)-dibenzo[b,f]pyrido[1,2-d]thiazepine-2-amine according to Formula I

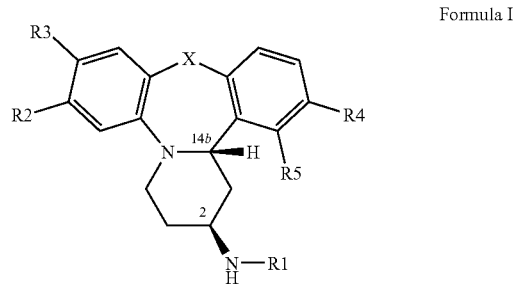

Formula I wherein
R1 is selected from the group consisting of (1-5C)acyl, (1-5C)thioacyl, (1-4C)alkylsulfonyl, and (1-4C)alkoxycarbonyl, each optionally substituted with one or more halogen atoms; and
R2 and R3 are each independently selected from the group consisting of H, halogen, cyano, nitro, and thiocarbamyl; and
R4 and R5 are each independently selected from the group consisting of H, (1-4C)alkyl, and (1-4C)alkoxy; and
X is selected from the group consisting of —O—, —S—, —SO—, and —SO$_2$—;
provided that, when R2 is Cl, R5 is not H or a racemate thereof.
2. The compound according to claim 1, wherein R1 is COCH$_3$.
3. The compound according to claim 1, wherein R1 is COCF$_3$.
4. The compound according to claim 1 wherein R2 is H.
5. The compound according to claim 1 wherein in that R2 is Cl.

6. The compound according to claim 1 wherein R2 is F.

7. The compound according to claim 1 wherein R3 is CN.

8. The compound according to claim 1 wherein R5 is methyl.

9. The compound according to claim 1 wherein R5 is methoxy.

10. The compound according to claim 1 wherein X is O.

11. The compound according to claim 10 wherein R1 is $COCF_3$, R2 is H, R3 is CN, R4 is H, and R5 is $CH_3$.

12. The compound according to claim 10 wherein R1 is COCF3, R2 is H, R3 is CN, R4 is H and R5 is $OCH_3$.

13. The compound according to claim 10 wherein R1 is $COCF_3$, R2 is F, R3 is CN, R4 is H, and R5 is $CH_3$.

14. A pharmaceutical composition comprising a compound according to claim 1 and a pharmaceutically acceptable carrier.

15. A method of contraception comprising administering a contraceptively effective amount of a compound according to claim 1 to a subject in need thereof.

16. A method of hormone replacement therapy comprising administering a pharmaceutically effective amount of a compound according to claim 1 to a subject in need thereof.

17. A method of treating a disorder selected from endometriosis, dysmenorrhea, and dysfunctional uterine bleeding, comprising administering a pharmaceutically effective amount of a compound according to claim 1 to a subject in need thereof.

* * * * *